(12) United States Patent
Fukuda

(10) Patent No.: US 12,249,046 B2
(45) Date of Patent: Mar. 11, 2025

(54) IMAGE PROCESSING APPARATUS, IMAGE PROCESSING METHOD, AND IMAGE PROCESSING PROGRAM

(71) Applicant: FUJIFILM Corporation, Tokyo (JP)

(72) Inventor: Wataru Fukuda, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 385 days.

(21) Appl. No.: 18/048,276

(22) Filed: Oct. 20, 2022

(65) Prior Publication Data
US 2023/0153969 A1 May 18, 2023

(30) Foreign Application Priority Data

Nov. 17, 2021 (JP) .................................. 2021-187371

(51) Int. Cl.
*G06T 5/50* (2006.01)
*A61B 6/42* (2024.01)
(Continued)

(52) U.S. Cl.
CPC .............. *G06T 5/50* (2013.01); *A61B 6/4291* (2013.01); *G06T 5/77* (2024.01); *G06T 7/60* (2013.01);
(Continued)

(58) Field of Classification Search
CPC .... G06T 5/50; G06T 5/77; G06T 7/60; G06T 7/70; G06T 2207/20224; A61B 6/4291;
(Continued)

(56) References Cited

U.S. PATENT DOCUMENTS

2021/0183062 A1    6/2021   Fukuda

FOREIGN PATENT DOCUMENTS

| EP | 2 236 085 A1 | 10/2010 | |
|---|---|---|---|
| JP | WO2020/059306 A1 | 8/2021 | |
| WO | WO-2012114757 A1 * | 8/2012 | ............. A61B 6/022 |

OTHER PUBLICATIONS

The extended European search report issued by the European Patent Office on Apr. 14, 2023, which corresponds to European Patent Application No. 22205422.3-1126 and is related to U.S. Appl. No. 18/048,276.

* cited by examiner

*Primary Examiner* — Matthew C Bella
*Assistant Examiner* — Janice E. Vaz
(74) *Attorney, Agent, or Firm* — Studebaker Brackett PLLC

(57) ABSTRACT

An image processing apparatus acquires a first low-energy image and a first high-energy image captured in a state in which a grid for removing scattered rays is inserted between a radiation source and a radiation detector, and the radiation source is disposed at a first position at which an incidence direction of radiation is a normal direction with respect to the grid, acquires a second low-energy image and a second high-energy image captured in a state in which the grid retreats from between the radiation source and the radiation detector, and the radiation source is disposed at a second position, estimates a thickness of the subject from the first low-energy image and the first high-energy image, and generates a difference image indicating a difference between the second high-energy image and the second low-energy image from the second low-energy image and the second high-energy image based on the thickness.

9 Claims, 16 Drawing Sheets

(51) Int. Cl.
*G06T 5/77* (2024.01)
*G06T 7/60* (2017.01)
*G06T 7/70* (2017.01)
*G06V 10/74* (2022.01)

(52) U.S. Cl.
CPC .............. *G06T 7/70* (2017.01); *G06V 10/761* (2022.01); *G06T 2207/20224* (2013.01)

(58) Field of Classification Search
CPC ......... A61B 6/022; A61B 6/025; A61B 6/502; A61B 6/5217; A61B 6/482; G06V 10/761
See application file for complete search history.

IMAGE PROCESSING APPARATUS, IMAGE PROCESSING METHOD, AND IMAGE PROCESSING PROGRAM

CROSS-REFERENCE TO RELATED APPLICATION

This application claims priority from Japanese Patent Application No. 2021-187371, filed Nov. 17, 2021, the disclosure of which is incorporated herein by reference in its entirety.

BACKGROUND

Technical Field

The present disclosure relates to an image processing apparatus, an image processing method, and a non-transitory storage medium storing an image processing program.

Related Art

A technology of performing contrast imaging of capturing a low-energy image and a high-energy image by irradiating a subject into which a contrast medium has been injected with radiation having different energies and generating a difference image indicating a difference between the high-energy image and the low-energy image to generate a radiation image in which the contrast medium is enhanced is known (see JPWO2020/059306A1, for example).

By the way, in a case in which imaging is performed without using a grid, there is a problem that an artifact component remains.

SUMMARY

The present disclosure has been made in consideration of the above circumstances, and is to provide an image processing apparatus, an image processing method, and a non-transitory storage medium storing an image processing program capable of obtaining a difference image in which a contrast medium is clearly reflected and an artifact component is suppressed.

In order to achieve the above object, a first aspect of the present disclosure relates to an image processing apparatus that processes a radiation image captured by a radiography apparatus including a radiation source and a radiation detector, the image processing apparatus including: at least one processor that is configured to: acquire a first low-energy image and a first high-energy image of a subject captured by the radiography apparatus in a state in which a grid for removing scattered rays is inserted between the radiation source and the radiation detector, and the radiation source is disposed at a first position at which an incidence direction of the radiation is a normal direction with respect to the grid; acquire a second low-energy image and a second high-energy image of the subject captured by the radiography apparatus in a state in which the grid retreats from between the radiation source and the radiation detector, and the radiation source is disposed at a second position different from the first position; estimate a thickness of the subject from the first low-energy image and the first high-energy image; and generate a difference image indicating a difference between the second high-energy image and the second low-energy image from the second low-energy image and the second high-energy image based on the estimated thickness, wherein the first and second low-energy images are captured by emitting radiation having first energy from the radiation source to the subject into which a contrast medium has been injected, and the first and second high-energy images are captured by emitting radiation having second energy higher than the first energy from the radiation source to the subject into which the contrast medium has been injected.

A second aspect of the present disclosure relates to the image processing apparatus according to the first aspect, in which the processor removes an artifact component from each of the second high-energy image and the second low-energy image, and generates the difference image from the second low-energy image and the second high-energy image from which the artifact components have been removed.

A third aspect of the present disclosure relates to the image processing apparatus according to the first aspect, in which the processor generates the difference image from the second low-energy image and the second high-energy image, and removes an artifact component from the difference image.

A fourth aspect of the present disclosure relates to the image processing apparatus according to any one of the first to third aspects, in which the processor estimates the thickness from a difference image indicating a difference between the first high-energy image and the first low-energy image.

A fifth aspect of the present disclosure relates to the image processing apparatus according to any one of the first to fourth aspects, in which the processor identifies a position of an object-of-interest dyed with the contrast medium in a depth direction from a difference image indicating a difference between the first high-energy image and the first low-energy image, and the difference image indicating the difference between the second high-energy image and the second low-energy image.

A sixth aspect of the present disclosure relates to the image processing apparatus according to any one of the first to fifth aspects, in which the artifact component is a component caused by oblique incidence of the radiation.

A seventh aspect of the present disclosure relates to the image processing apparatus according to any one of the first to fifth aspects, in which the artifact component is a scattered ray component caused by the scattered ray.

In addition, in order to achieve the above object, an eighth aspect of the present disclosure relates to an image processing method in which a computer executes image processing of a radiation image captured by a radiography apparatus including a radiation source and a radiation detector, the image processing method including: acquiring a first low-energy image and a first high-energy image of a subject captured by the radiography apparatus in a state in which a grid for removing scattered rays is inserted between the radiation source and the radiation detector, and the radiation source is disposed at a first position at which an incidence direction of the radiation is a normal direction with respect to the grid; acquiring a second low-energy image and a second high-energy image of the subject captured by the radiography apparatus in a state in which the grid retreats from between the radiation source and the radiation detector, and the radiation source is disposed at a second position different from the first position; estimating a thickness of the subject from the first low-energy image and the first high-energy image; and generating a difference image indicating a difference between the second high-energy image and the second low-energy image from the second low-energy image and the second high-energy image based on the estimated thickness, wherein the first and second low-energy images are captured by emitting radiation having first energy from the radiation source to the subject into which a contrast medium has been injected, and the first and second high-energy images are captured by emitting radiation having second energy higher than the first energy from the radiation source to the subject into which the contrast medium has been injected.

In addition, in order to achieve the above object, a ninth aspect of the present disclosure relates to a non-transitory storage medium storing an image processing program causing a computer to execute image processing of a radiation image captured by a radiography apparatus including a radiation source and a radiation detector, the image processing including: acquiring a first low-energy image and a first high-energy image of a subject captured by the radiography apparatus in a state in which a grid for removing scattered rays is inserted between the radiation source and the radiation detector, and the radiation source is disposed at a first position at which an incidence direction of the radiation is a normal direction with respect to the grid; acquiring a second low-energy image and a second high-energy image of the subject captured by the radiography apparatus in a state in which the grid retreats from between the radiation source and the radiation detector, and the radiation source is disposed at a second position different from the first position; estimating a thickness of the subject from the first low-energy image and the first high-energy image; and generating a difference image indicating a difference between the second high-energy image and the second low-energy image from the second low-energy image and the second high-energy image based on the estimated thickness, wherein the first and second low-energy images are captured by emitting radiation having first energy from the radiation source to the subject into which a contrast medium has been injected, and the first and second high-energy images are captured by emitting radiation having second energy higher than the first energy from the radiation source to the subject into which the contrast medium has been injected.

According to the present disclosure, it is possible to obtain the difference image in which the contrast medium is clearly reflected and the artifact component is suppressed.

DETAILED DESCRIPTION

In the following, an embodiment of the present invention will be described in detail with reference to the drawings. It should be noted that the embodiment does not limit the present invention.

Figure 1:
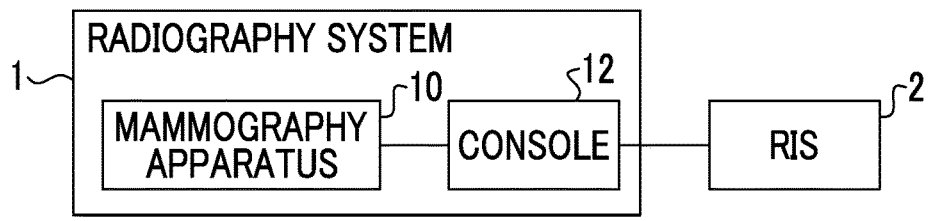
FIG. 1 is a configuration diagram schematically showing an example of an overall configuration of a radiography system according to an embodiment.

First, an example of an overall configuration of a radiography system according to the present embodiment will be described. FIG. 1 shows a configuration diagram showing an example of an overall configuration of a radiography system 1 according to the present embodiment. As shown in FIG. 1, the radiography system 1 according to the present embodiment comprises a mammography apparatus 10 and a console 12. The mammography apparatus 10 according to the present embodiment is an example of a radiography apparatus according to the present disclosure. In addition, the console 12 according to the present embodiment is an example of an image processing apparatus according to the present disclosure.

Figure 2:
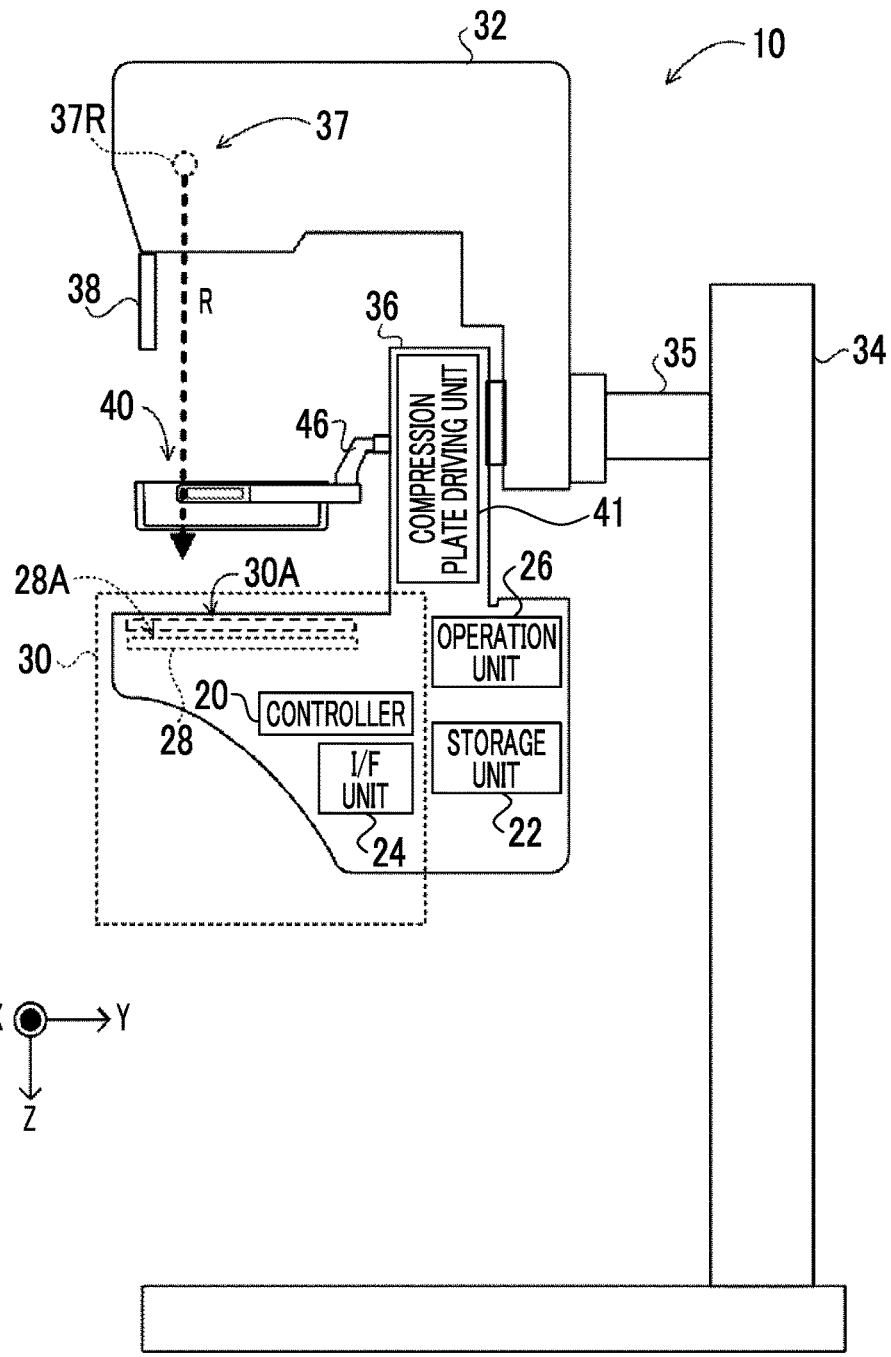
FIG. 2 is a side view showing an example of an appearance of a mammography apparatus according to the embodiment.

First, the mammography apparatus 10 according to the present embodiment will be described. FIG. 2 shows a side view showing an example of an appearance of the mammography apparatus 10 according to the present embodiment. It should be noted that FIG. 2 shows the example of the appearance of the mammography apparatus 10 as viewed from a right side of an examinee.

The mammography apparatus 10 according to the present embodiment is an apparatus that uses a breast of the examinee as a subject and captures a radiation image of the breast by irradiating the breast with radiation R (for example, X-rays). It should be noted that the mammography apparatus 10 may be an apparatus that images the breast of the examinee in a state in which the examinee is sitting on a chair (including a wheelchair) or the like (sitting state) in addition to a state in which the examinee is standing (standing state).

An operation unit 26 is provided as a plurality of switches on an imaging table 30 of the mammography apparatus 10, for example. It should be noted that the operation unit 26 may be provided as a touch panel type switch, or may be provided as a foot switch operated by a user, such as a doctor or an engineer with a foot.

As shown in FIG. 2, the mammography apparatus 10 according to the present embodiment comprises a controller 20, a storage unit 22, and an interface (I/F) unit 24 inside the imaging table 30, which will be described below in detail.

In addition, as shown in FIG. 2, a radiation detector 28 is disposed inside the imaging table 30. In the mammography apparatus 10 according to the present embodiment, the user positions the breast of the examinee on an imaging surface 30A of the imaging table 30 during the imaging. The radiation detector 28 detects the radiation R transmitted through the breast of the examinee and the imaging table 30, generates a radiation image based on the detected radiation R, and outputs image data representing the generated radiation image. A type of the radiation detector 28 according to the present embodiment is not particularly limited. For example, a radiation detector of an indirect conversion method that converts the radiation R into light and converts the converted light into a charge may be used, and a radiation detector of a direct conversion method that directly converts the radiation R into a charge may be used.

Figure 3:
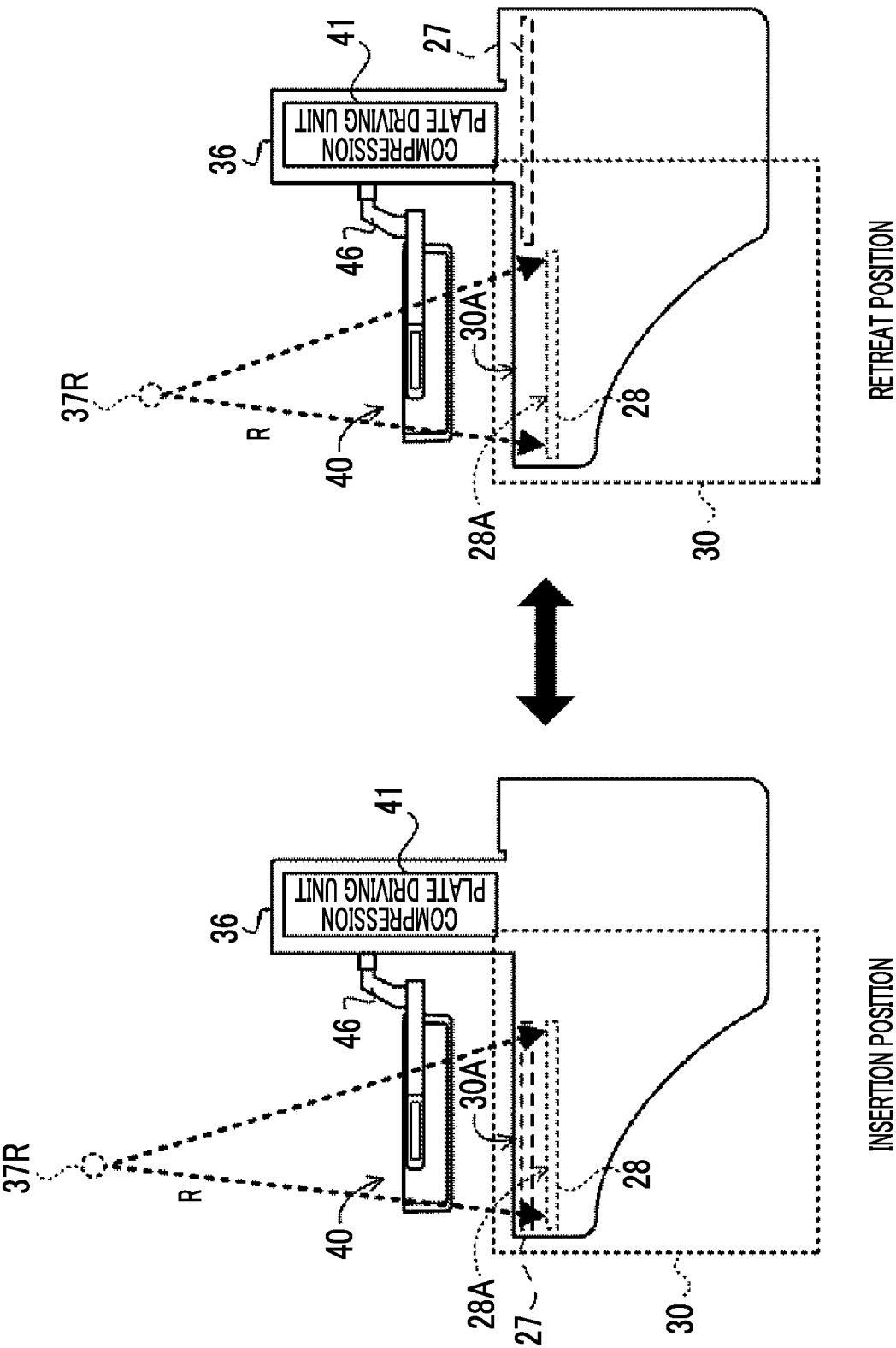
FIG. 3 is a diagram for describing movement of a grid according to the embodiment.

In addition, a grid 27 is provided between a radiation source 37R and the radiation detector 28 to remove scattered rays. As shown in FIG. 3, the grid 27 according to the present embodiment can be moved between a position (hereinafter, referred to as "insertion position") at which the grid 27 is inserted between the radiation source 37R and the radiation detector 28, and a position (hereinafter, referred to as "retreat position") at which the grid 27 retreats from between the radiation source 37R and the radiation detector 28 by a grid movement unit 31 (see FIG. 5). As an example, in the mammography apparatus 10 according to the present embodiment, as shown in FIG. 3, the grid 27 is slid in a direction of a compression unit 36 to be moved from the insertion position to the retreat position.

Figure 4A:
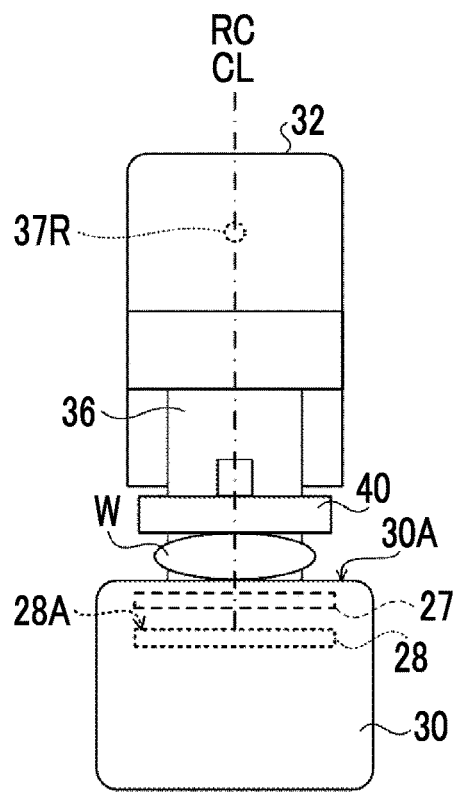
FIG. 4A is a diagram for describing a position of a radiation source in first contrast imaging.
Figure 4B:
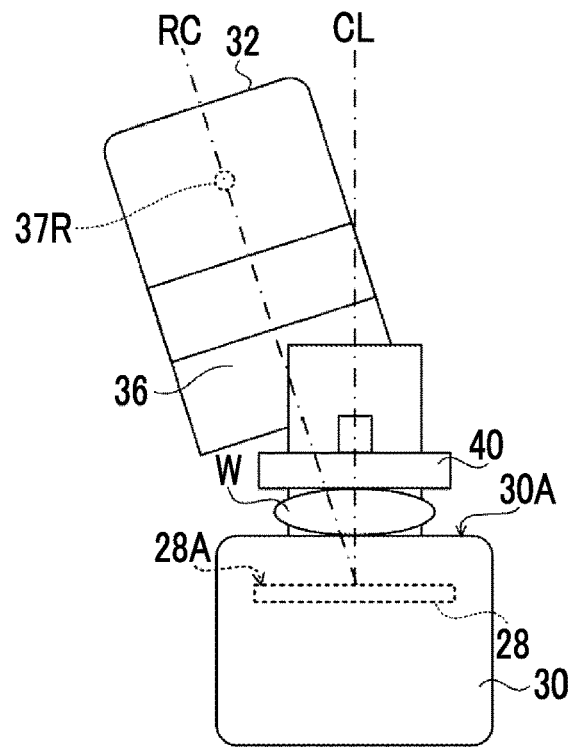
FIG. 4B is a diagram for describing the position of the radiation source in second contrast imaging.

As shown in FIG. 3, at the insertion position, specifically, the grid 27 is disposed substantially parallel to the radiation detector 28 between the imaging surface 30A of the imaging table 30 and the radiation detector 28, and a normal line with respect to a detection surface 28A of the radiation detector 28 and a normal line of the grid 27 are the same (see normal line CL in FIGS. 4A and 4B). At the insertion position, the radiation detector 28 is irradiated with the radiation R emitted from the radiation source 37R via the grid 27. On the other hand, at the retreat position, as shown in FIG. 3, the radiation detector 28 is irradiated with the radiation R emitted from the radiation source 37R without passing through the grid 27.

A radiation emitting unit 37 comprises the radiation source 37R. As shown in FIG. 2, the radiation emitting unit 37 is provided in an arm part 32 together with the imaging table 30 and the compression unit 36. As shown in FIG. 2, a face guard 38 is attachably and detachably provided at a position near the examinee on the arm part 32 below the radiation emitting unit 37. The face guard 38 is a protective member for protecting the examinee from the radiation R emitted from the radiation source 37R.

It should be noted that, as shown in FIG. 2, the mammography apparatus 10 according to the present embodiment comprises the arm part 32, a base 34, and a shaft part 35. The arm part 32 is held by the base 34 to be movable in a vertical direction (Z-axis direction). In addition, the arm part 32 can be rotated with respect to the base 34 by the shaft part 35. The shaft part 35 is fixed to the base 34, and the shaft part 35 and the arm part 32 are rotated together.

A gear is provided for each of the shaft part 35 and the compression unit 36. By switching between an engaged state and a non-engaged state of the gears, a state in which the compression unit 36 and the shaft part 35 are connected and are integrally rotated and a state in which the shaft part 35 is separated from the compression unit 36 and the imaging table 30 and is idled can be switched. It should be noted that, for switching between transmission and non-transmission of power of the shaft part 35, various mechanical elements can be used in addition to the gear described above.

The arm part 32, the imaging table 30, and the compression unit 36 can be separately rotated relative to the base 34 with the shaft part 35 as a rotation axis. In the present embodiment, the base 34, the arm part 32, the imaging table 30, and the compression unit 36 are each provided with an engaging part (not shown), and each of the arm part 32, the imaging table 30, and the compression unit 36 is connected to the base 34 by switching a state of the engaging part. One or two of the arm part 32, the imaging table 30, or the compression unit 36, which are connected to the shaft part 35, are integrally rotated around the shaft part 35.

The compression unit 36 is provided with a compression plate driving unit 41 that moves the compression plate 40 in the vertical direction (Z-axis direction). The compression plate 40 according to the present embodiment has a function of compressing the breast of the examinee. A support part 46 of the compression plate 40 is attachably and detachably attached to the compression plate driving unit 41, is moved in the vertical direction (Z-axis direction) by the compression plate driving unit 41, and compresses the breast of the examinee with the imaging table 30.

The mammography apparatus 10 according to the present embodiment has a function of performing general imaging and a function of performing so-called contrast imaging in which the imaging is performed in a state in which a contrast medium has been injected into the breast of the examinee. In the present embodiment, the "contrast imaging" refers to the imaging performed in a state in which the contrast medium is injected into the breast (subject 9) of the examinee, and the "general imaging" refers to imaging that is not the contrast imaging.

It should be noted that the mammography apparatus 10 according to the present embodiment has a contrast enhanced digital mammography (CEDM) function of performing the contrast imaging by energy subtraction imaging as the function of performing the contrast imaging.

In addition, the mammography apparatus 10 according to the present embodiment has a function of performing, as the contrast imaging, so-called stereo imaging in which two types of the contrast imaging of first contrast imaging and second contrast imaging in which a position of the radiation source 37R varies are performed. Two types of the contrast imaging will be described with reference to FIGS. 4A and 4B.

As shown in FIG. 4A, the first contrast imaging is the contrast imaging performed with the radiation source 37R at a first position at which an incidence direction of the radiation R is a normal direction with respect to the grid 27 and the radiation detector 28. That is, in the first contrast imaging, the normal line CL with respect to the grid 27 and the detection surface 28A of the radiation detector 28 matches a radiation axis RC. In the first contrast imaging, a first low-energy image is captured by irradiating a breast W into which the contrast medium has been injected with the radiation R having first energy. In addition, in the first contrast imaging, a first high-energy image is captured by emitting the radiation R having second energy higher than the first energy. It should be noted that, in the present embodiment, the radiation image captured by emitting the radiation R having the first energy is referred to as a "low-energy image", and the radiation image captured by emitting the radiation R having the second energy is referred to as a "high-energy image". In addition, in a case in which the low-energy image, the high-energy image, and a difference image described below generically refer to a mammography image obtained by the mammography apparatus 10 without distinguishing the types thereof, the low-energy image, the high-energy image, and the difference image are simply referred to as a "radiation image"

For example, an iodine contrast medium with a k-absorption edge of 32 keV is generally used as the contrast medium for the contrast imaging. In the contrast imaging in this case, the low-energy image is captured by emitting the radiation R having the first energy lower than the k-absorption edge of the iodine contrast medium. In addition, the high-energy image is captured by emitting the radiation R having the second energy higher than the k-absorption edge of the iodine contrast medium.

The contrast medium and a body tissue, such as a mammary gland, have different absorption characteristics of the radiation. Therefore, in the high-energy image captured as described above, the body tissue, such as the mammary gland or fat, is reflected, and the contrast medium is clearly reflected. In addition, in the low-energy image, almost no contrast medium is reflected, and the body tissue, such as the mammary gland, is clearly reflected. Therefore, the difference image indicating a difference between the low-energy image and the high-energy image can be an image in which a mammary gland structure has been removed and the contrast medium is clearly reflected.

As shown in FIG. 4A, in a case of performing the first contrast imaging, the grid 27 is at the insertion position, and the grid 27 is inserted between the radiation source 37R and the radiation detector 28. In a case in which the grid 27 is at the insertion position, the detection surface 28A of the radiation detector 28 is irradiated with the radiation R emitted from the radiation source 37R and transmitted through the breast W via the grid 27. Therefore, the radiation image obtained by the radiation detector 28 is an image in which a scattered ray component caused by the scattered ray and the component caused by the oblique incidence of the radiation are suppressed by the grid 27. Therefore, the first low-energy image and the first high-energy image are images in which an artifact component including the scattered ray component and the component caused by the oblique incidence of the radiation are suppressed.

On the other hand, as shown in FIG. 4B, the second contrast imaging is the contrast imaging with the radiation source 37R at a position different from the first position. In other words, the second contrast imaging is the contrast imaging performed by causing the radiation R emitted from the radiation source 37R to be obliquely incident on the detection surface 28A of the radiation detector 28. That is, in the second contrast imaging, the normal line CL of the detection surface 28A of the radiation detector 28 and the radiation axis RC do not match. In the second contrast imaging, a second low-energy image is captured by irradiating the breast W into which the contrast medium has been injected with the radiation R having the first energy. In addition, in the second contrast imaging, a second high-energy image is captured by emitting the radiation R having the second energy.

As shown in FIG. 4B, in a case of performing the second contrast imaging, the grid 27 is at the retreat position, and the grid 27 retreats from between the radiation source 37R and the radiation detector 28. In a case in which the grid 27 is at the retreat position, the detection surface 28A of the radiation detector 28 is irradiated with the radiation R emitted from the radiation source 37R and transmitted through the breast W without passing through the grid 27. Therefore, the radiation image obtained by the radiation detector 28 is an image in which the scattered ray component caused by the scattered rays and the oblique incidence component caused by the oblique incidence of the radiation are included. Therefore, the second low-energy image and the second high-energy image are images including the scattered ray component and the oblique incidence component, which are the artifact component. Such an artifact component appears as an image that appears white in the radiation image.

Such an artifact component will be described. As described above, the artifact component mainly includes the scattered ray component and the oblique incidence component caused by the oblique incidence of the radiation.

Figure 5A:
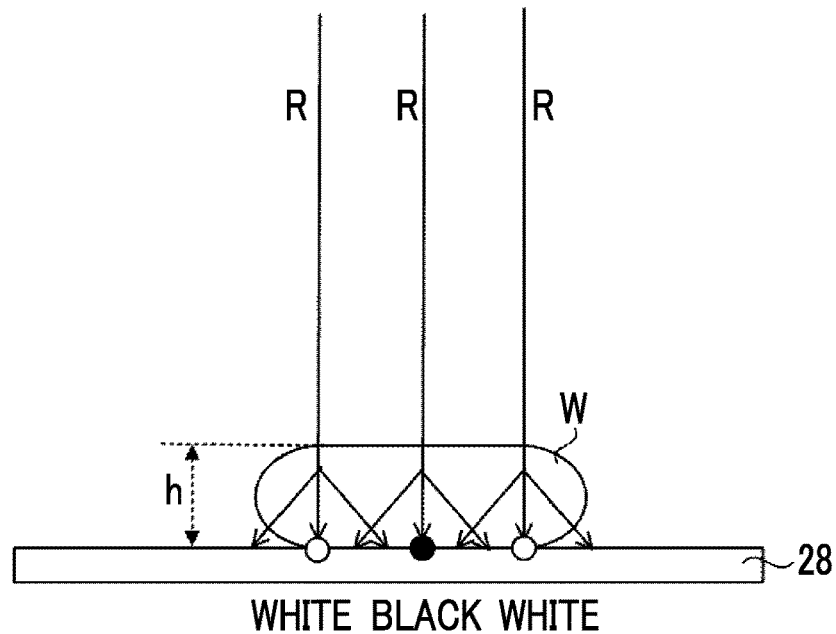
FIG. 5A is a diagram for describing a scattered ray component.

First, with reference to FIG. 5A, the scattered ray component caused by the scattered rays of the radiation R will be described. FIG. 5A shows a schematic diagram for describing an example of an artifact due to the scattered ray component of the radiation R. An image of an inside region of the breast W has a large dose because the scattered rays generated by the breast W overlap each other. Therefore, the image of the inside region of the breast W has a large pixel value and the image is black. On the other hand, in the image of an end part region of the breast W, a part of the scattered rays escapes to an outside of the breast W, so that the dose is reduced. Therefore, a cool image on an end part side of the breast W, in other words, on a skin line side, has a small pixel value and a small image. In other words, in the vicinity of the skin line of the breast W, the pixel value is smaller than in the inside region. In a case of the breast W, since the scattered rays are less likely to escape to the outside on a chest wall side, the dose is increased and the pixel value is increased, so the image tends to be black. On the other hand, since the scattered rays are more likely to escape to the outside on a nipple side, the dose is decreased and the pixel value is decreased, so that the image tends to be white. Therefore, the scattered ray component of the radiation R is the artifact component. It should be noted that an amount of the generated scattered rays are larger as a thickness h of the breast W is larger.

Figure 5B:
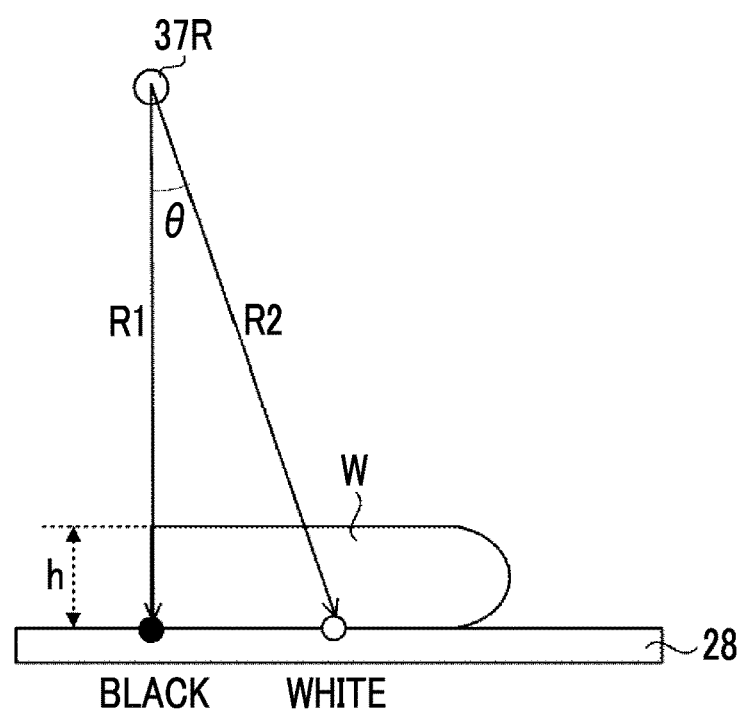
FIG. 5B is a diagram for describing an oblique incidence component.

Next, with reference to FIG. 5B, the oblique incidence component caused by the oblique incidence of the radiation R on the breast W will be described. FIG. 5B shows a schematic diagram for describing an example of the artifact due to the oblique incidence component of the radiation R. In a case in which radiation R1 having an incidence angle of 0 degrees is incident on the breast W having the thickness h from the radiation source 37R, a length of a transmission path through which the radiation R1 is transmitted through the breast Wish. On the other hand, in a case in which radiation R2 having an incidence angle θ is incident from the radiation source 37R, the length of the transmission path is h/cosθ. Therefore, the transmission path in a case in which the radiation R2 is incident is longer than the transmission path in a case in which the radiation R1 is incident by a length x represented by Expression (1).

$$x=(1/\cos \theta-1)\times h \qquad (1)$$

As the transmission path is longer, the dose of the radiation R reaching the radiation detector 28 is smaller. Therefore, the radiation R2 that is transmitted through the breast W and reaches the radiation detector 28 has a smaller dose than the radiation R1. Due to the smaller dose, the image generated by the radiation detector 28 in response to the radiation R2 will be whiter than the image generated by the radiation detector 28 in response to the radiation R1. As shown in Expression (1), the pixel value of the radiation image is decreased due to the oblique incidence of the radiation R. In addition, as the thickness h of the breast W is thicker, the transmission path is longer and the pixel value of the radiation image is smaller. Therefore, the oblique incidence component of the radiation R is the artifact component.

Figure 6:
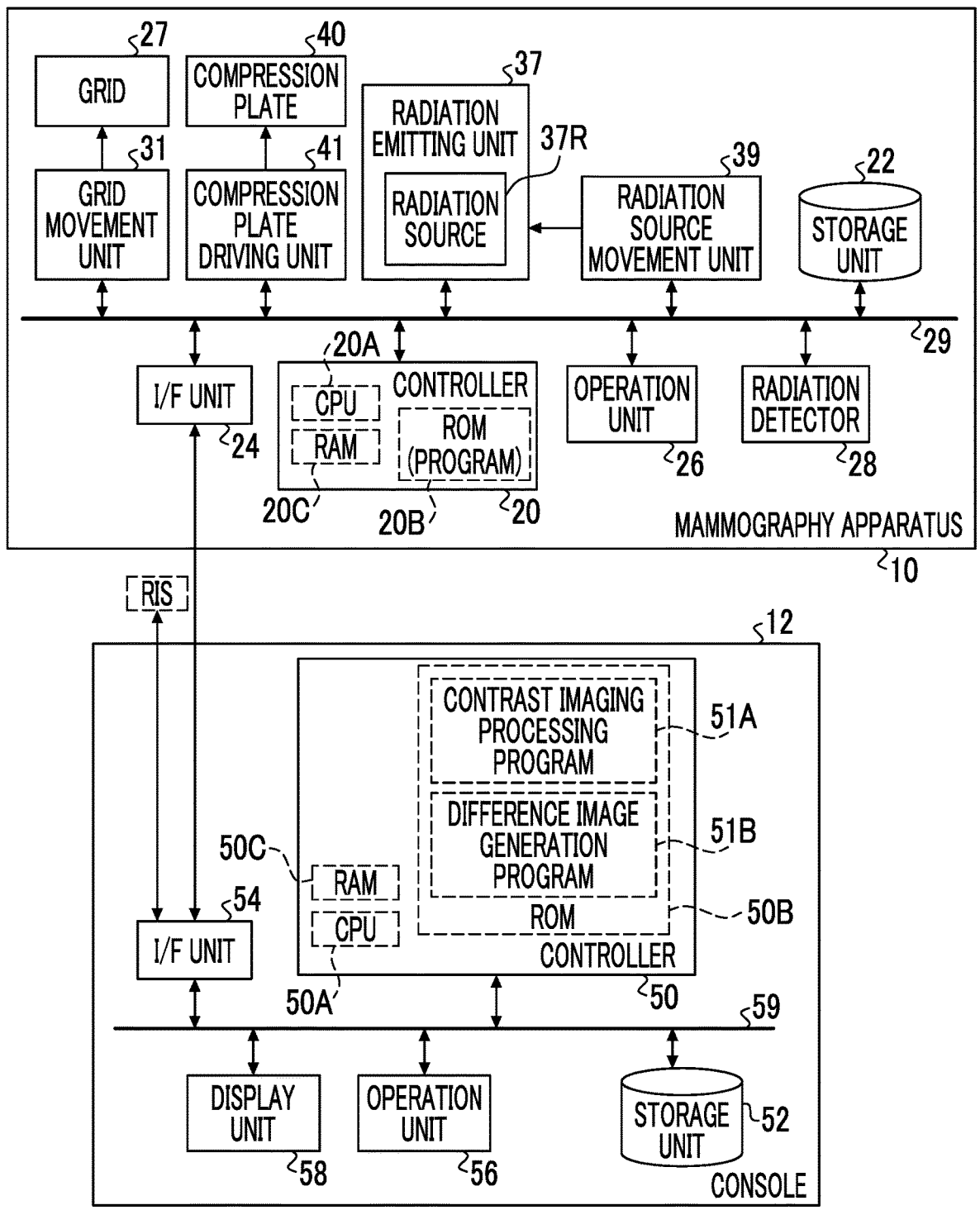
FIG. 6 is a block diagram showing an example of configurations of the mammography apparatus and a console according to the embodiment.

Further, configurations of the mammography apparatus 10 and the console 12 will be described with reference to FIG. 6. FIG. 6 shows a block diagram showing an example of the configurations of the mammography apparatus 10 and the console 12 according to the present embodiment. As shown in FIG. 6, in the mammography apparatus 10 according to the present embodiment, the controller 20, the storage unit 22, the I/F unit 24, the operation unit 26, the grid movement unit 31, a radiation source movement unit 39, and the compression plate driving unit 41 are connected to each other via a bus 29, such as a system bus or a control bus, such that various types of information can be exchanged.

The controller 20 controls an overall operation of the mammography apparatus 10 under the control of the console 12. The controller 20 comprises a central processing unit (CPU) 20A, a read only memory (ROM) 20B, and a random access memory (RAM) 20C. The ROM 20B stores, in advance, various programs, including an imaging processing program for controlling radiation image capturing, which is executed by the CPU 20A. The RAM 20C transitorily stores various data.

The storage unit 22 stores the image data of the radiation image captured by the radiation detector 28 or various types of other information. Specific examples of the storage unit 22 include a hard disk drive (HDD) and a solid state drive (SSD). The I/F unit 24 performs communication of various types of information with the console 12 by wireless communication or wired communication. The image data of the radiation image captured by the radiation detector 28 in the mammography apparatus 10 is transmitted to the console 12 via the I/F unit 24 by wireless communication or wired communication.

The grid movement unit 31 has a function of moving the grid 27 between the insertion position and the retreat position in accordance with an instruction from the controller 20, as described above. The radiation source movement unit 39 has a function of rotating the arm part 32 by rotating the shaft part 35 to move the position of the radiation source 37R from the first position to a second position or from the second position to the first position. The compression plate driving unit 41 has a function of moving the compression plate 40 in the vertical direction (from a direction of compressing the breast to a direction away from the breast), as described above.

On the other hand, the console 12 according to the present embodiment has a function of controlling the mammography apparatus 10 by using an imaging order and various types of information acquired from a radiology information system (RIS) 2 via a wireless communication local area network (LAN) and the like, and an instruction performed by the user by an operation unit 56 and the like.

The console 12 according to the present embodiment is, for example, a server computer. As shown in FIG. 5, the console 12 comprises a controller 50, a storage unit 52, an I/F unit 54, the operation unit 56, and a display unit 58. The controller 50, the storage unit 52, the I/F unit 54, the operation unit 56, and the display unit 58 are connected to each other via a bus 59, such as a system bus or a control bus, such that various types of information can be exchanged.

The controller 50 according to the present embodiment controls an overall operation of the console 12. The controller 50 comprises a CPU 50A, a ROM 50B, and a RAM 50C. The ROM 50B stores, in advance, various programs including a contrast imaging processing program 51A and a difference image generation program 51B, which are executed by the CPU 50A and will be described below. The RAM 50C transitorily stores various data. The CPU 50A according to the present embodiment is an example of a processor according to the present disclosure. The difference image generation program 51B according to the present embodiment is an example of an image processing program according to the present disclosure.

The storage unit 52 stores the image data of the radiation image captured by the mammography apparatus 10 and various types of other information. Specific examples of the storage unit 52 include an HDD and an SSD.

The operation unit 56 is used by the user to input the instruction, various types of information, and the like related to the radiation image capturing and the like, including an irradiation instruction of the radiation R. The operation unit 56 is not particularly limited, and examples thereof include various switches, a touch panel, a touch pen, and a mouse. The display unit 58 displays various types of information. It should be noted that the operation unit 56 and the display unit 58 may be integrated to form a touch panel display.

The I/F unit 54 performs communication of various types of information between the mammography apparatus 10 and the RIS 2 by wireless communication or wired communication. In the radiography system 1 according to the present embodiment, the console 12 receives the image data of the radiation image captured by the mammography apparatus 10 from the mammography apparatus 10 via the I/F unit 54 by wireless communication or wired communication.

Figure 7:
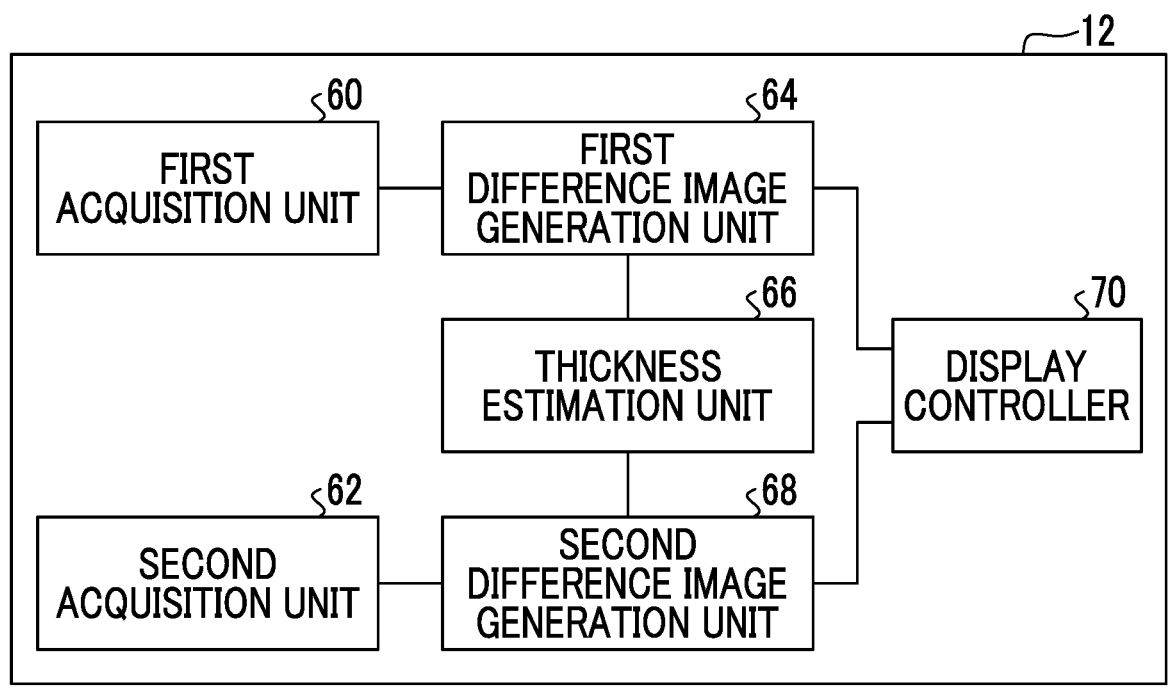
FIG. 7 is a functional block diagram showing an example of a function of the console according to the embodiment.

Further, FIG. 7 shows a functional block diagram of an example of the configuration of the console 12 according to the present embodiment. As shown in FIG. 7, the console 12 comprises a first acquisition unit 60, a second acquisition unit 62, a first difference image generation unit 64, a thickness estimation unit 66, a second difference image generation unit 68, and a display controller 70. As an example, in the console 12 according to the present embodiment, the CPU 50A of the controller 50 executes the difference image generation program 51B stored in the ROM 50B, so that the CPU 50A functions as the first acquisition unit 60, the second acquisition unit 62, the first difference image generation unit 64, the thickness estimation unit 66, the second difference image generation unit 68, and the display controller 70.

The first acquisition unit 60 has a function of acquiring the first low-energy image and the first high-energy image obtained by the first contrast imaging. Specifically, the first acquisition unit 60 acquires image data representing the first low-energy image and image data representing the first high-energy image captured in the first contrast imaging by the radiation detector 28 of the mammography apparatus 10 via the I/F unit 24 and the I/F unit 54. The first acquisition unit 60 outputs the acquired first low-energy image and first high-energy image to the first difference image generation unit 64.

The first difference image generation unit 64 has a function of generating a first difference image indicating a difference between the first high-energy image and the first low-energy image. As an example, the first difference image generation unit 64 according to the present embodiment generates image data of the first difference image by subtracting image data obtained by multiplying the first low-energy image by a predetermined coefficient from image data obtained by multiplying the first high-energy image by a predetermined coefficient for each corresponding pixel. As an example of a weighting coefficient, a weighting coefficient based on an absorption coefficient $\mu g^L$ of the mammary gland for the radiation R having the first energy, an absorption coefficient $\mu g^L$ of the fat for the radiation R having the first energy, an absorption coefficient $\mu g^H$ of the mammary gland for the radiation R having the second energy, and an absorption coefficient $\mu g^H$ of the fat for the radiation R having the second energy is used. Specifically, a weighting coefficient $\gamma$ obtained by Expression (2) is used.

$$\gamma = (\mu g^L - \mu a^L)/(\mu g^H - \mu a^H) \quad (2)$$

The first difference image is an image in which a mammary gland tissue has been removed and the contrast medium is enhanced. The first difference image generation unit 64 outputs the generated first difference image to the thickness estimation unit 66 and the display controller 70.

The thickness estimation unit 66 has a function of estimating the thickness of the breast from the first low-energy image and the first high-energy image. In other words, the thickness estimation unit 66 has a function of estimating the thickness of the breast in a state of being compressed by the compression plate 40 based on the first difference image. As an example, the thickness estimation unit 66 according to the present embodiment derives the thickness of the breast W by calculating a coefficient that eliminates the contrast between the mammary gland and the fat. As a specific method, for example, a method disclosed in JP6667462B can be applied. It should be noted that the method of estimating the thickness of the breast by the thickness estimation unit 66 is not limited to the present form, and an existing method can be used. For example, as disclosed in JP2007-300964A, the thickness of the breast may be estimated by simulating radiation scattering based on thickness information and density distribution of the subject. The thickness estimation unit 66 outputs the estimated thickness of the breast to the second difference image generation unit 68.

In addition, the second acquisition unit 62 has a function of acquiring the second low-energy image and the second high-energy image obtained by the second contrast imaging. Specifically, the second acquisition unit 62 acquires image data representing the second low-energy image and image data representing the second high-energy image captured in the second contrast imaging by the radiation detector 28 of the mammography apparatus 10 via the I/F unit 24 and the I/F unit 54. The second acquisition unit 62 outputs the acquired second low-energy image and second high-energy image to the second difference image generation unit 68.

A second difference image generation unit 68 has a function of generating a second difference image indicating a difference between the second high-energy image and the second low-energy image in which the artifact components are suppressed, based on the thickness of the breast estimated by the thickness estimation unit 66. As an example, the second difference image generation unit 68 according to the present embodiment generates the second difference image from the second low-energy image and the second high-energy image by the same method as the method of generating the first difference image by the first difference image generation unit 64 as described above. In addition, the second difference image generation unit 68 removes the artifact component described above from the generated second difference image based on the thickness of the breast estimated by the thickness estimation unit 66. Although the method of removing the artifact component from the second difference image by the second difference image generation unit 68 is not particularly limited, as an example, the second difference image generation unit 68 according to the present embodiment removes the scattered ray component and the oblique incidence component by applying a low-frequency removal filter corresponding to the scattered ray component and the oblique incidence component corresponding to the thickness of the breast to the second difference image.

The scattered ray component and the oblique incidence component are generated as low-frequency unevenness. Therefore, by applying the low-frequency removal filter that removes a low-frequency component corresponding to the scattered ray component and the oblique incidence component to the second difference image, the scattered ray component and the oblique incidence component have been removed from the second difference image. It should be noted that a degree of the scattered ray component and the oblique incidence component varies in accordance with the thickness of the breast. Specifically, as the breast is thicker, the scattered ray component and the oblique incidence component are larger. Therefore, it is preferable to apply the low-frequency removal filter that removes a lower-frequency component as the breast is thicker. The second difference image generation unit 68 according to the present embodiment prepares a plurality of low-frequency removal filters corresponding to the thickness of the breast. Then, the second difference image generation unit 68 applies the low-frequency removal filter corresponding to the thickness of the breast estimated by the thickness estimation unit 66 to remove the scattered ray component and the oblique incidence component from the second difference image. It should be noted that a threshold value of the low-frequency removal filter may be changeable in accordance with the scattered ray component, the oblique incidence component, the instruction of the user, or the like. As described above, the second difference image generation unit 68 generates the second difference image in which the artifact component is suppressed. The second difference image generation unit 68 outputs the generated second difference image to the display controller 70.

The display controller 70 has a function of displaying the first difference image and the second difference image on the display unit 58.

Next, an action of the console 12 in the contrast imaging by the radiography system 1 according to the present embodiment will be described with reference to the drawings.

Figure 8:
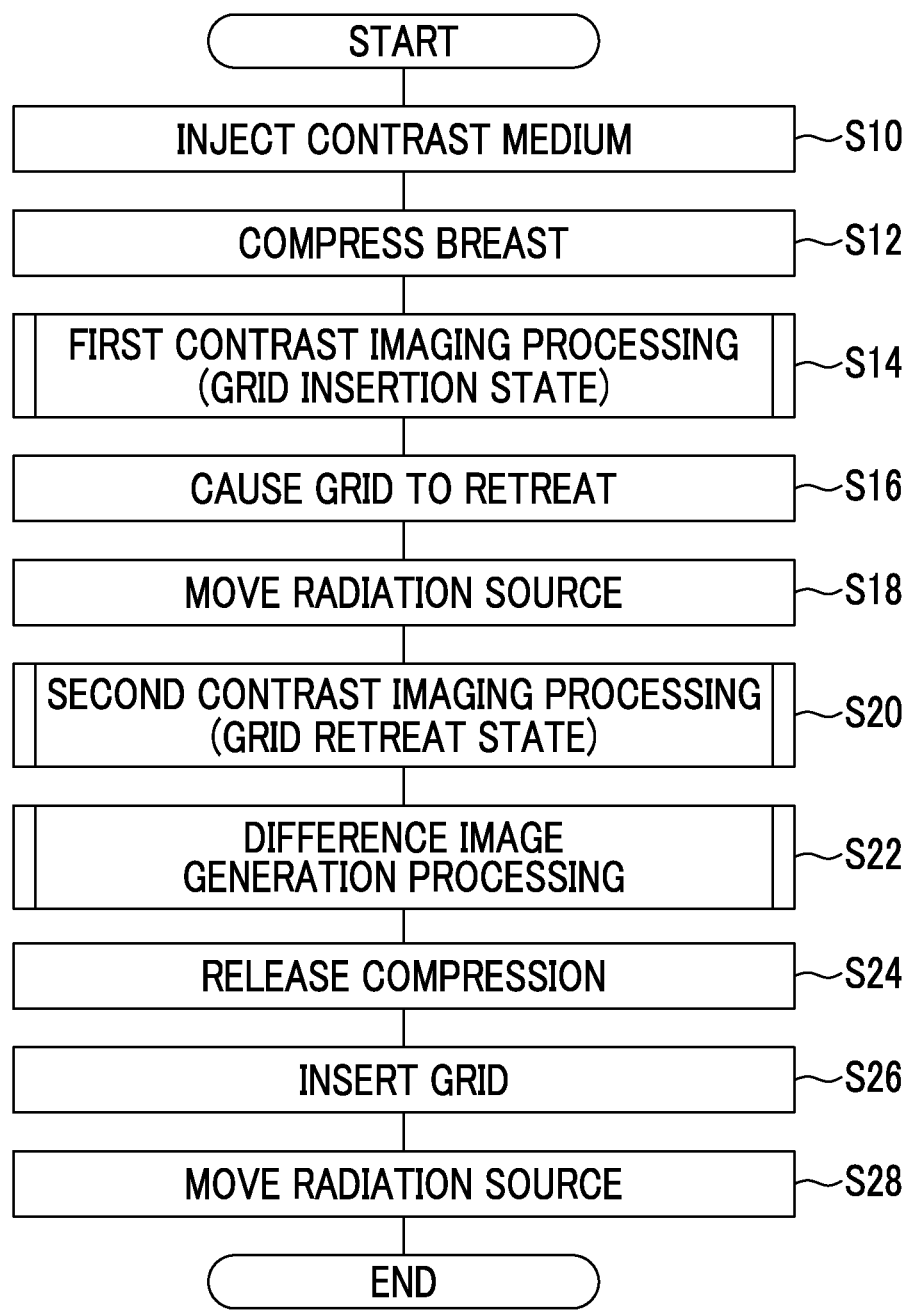
FIG. 8 is a flowchart showing an example of a flow of contrast imaging by the radiography system according to the embodiment.

FIG. 8 shows a flowchart showing an example of a flow of the contrast imaging by the radiography system 1 according to the present embodiment. In a case in which the contrast imaging is performed, first, the user injects the contrast medium into the breast, which is the subject, as shown in step S10 of FIG. 8. Next, as shown in step S12, the user positions the breast of the examinee on the imaging table 30 of the mammography apparatus 10 and compresses the breast with the compression plate 40.

Figure 9:
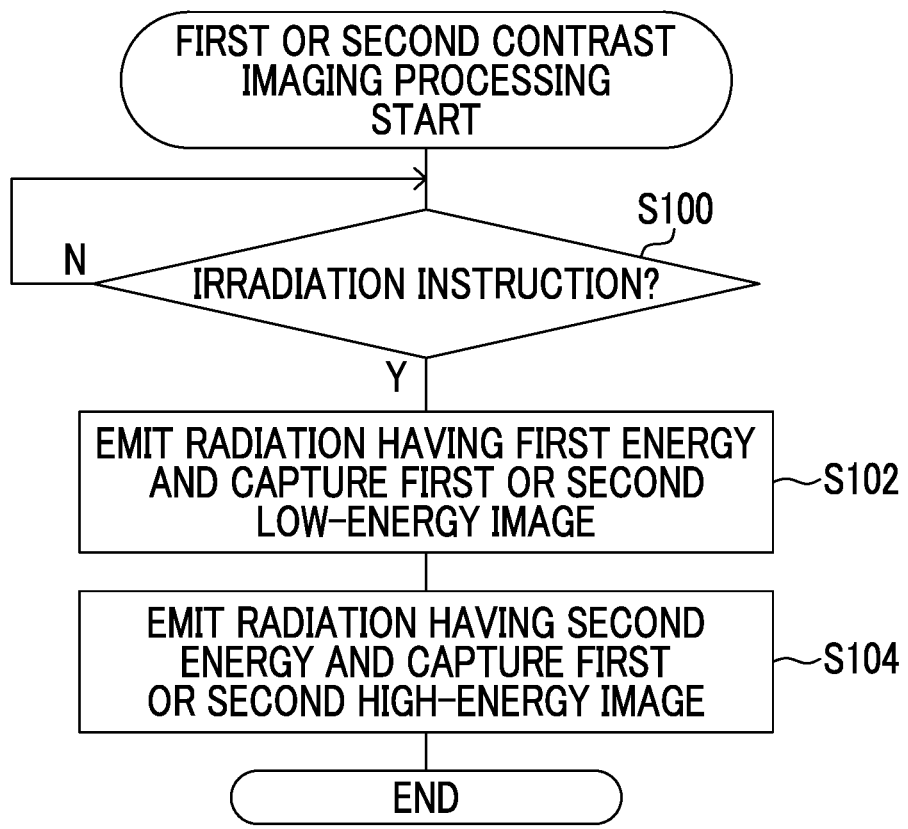
FIG. 9 is a flowchart showing an example of a flow of contrast imaging processing executed in the contrast imaging according to the embodiment.

Next, in step S14, the console 12 performs first contrast imaging processing shown in FIG. 9 for performing the first contrast imaging described above by the mammography apparatus 10. It should be noted that, since the first contrast imaging processing and second contrast imaging processing, which will be described below in detail, are the same processing, both the first contrast imaging processing and the second contrast imaging processing will be described with reference to FIG. 9.

As described above, in the first contrast imaging (see FIGS. 3 and 4A), the grid 27 is at the insertion position, and the grid 27 is inserted between the radiation source 37R and the detection surface 28A of the radiation detector 28.

In the console 12 according to the present embodiment, as an example, the CPU 50A of the controller 50 executes the contrast imaging processing program 51A stored in the ROM 50B, thereby executing the first contrast imaging processing whose example is shown in FIG. 9. FIG. 9 shows a flowchart showing an example of a flow of the first contrast imaging processing executed in the console 12 according to the present embodiment.

In step S100 of FIG. 9, the controller 50 determines whether or not the irradiation instruction of the radiation R is received. A negative determination is made in the determination in step S100 until the irradiation instruction is received. On the other hand, in a case in which the irradiation instruction is received, a positive determination is made in the determination in step S100, and the processing proceeds to step S102.

In step S102, the controller 50 outputs the instruction to emit the radiation R having the first energy to the mammography apparatus 10. In the mammography apparatus 10, the controller 20 emits the radiation R having the first energy from the radiation source 37R toward the breast based on the instruction input from the console 12, and the first low-energy image is captured by the radiation detector 28.

In next step S104, the controller 50 outputs the instruction to emit the radiation R having the second energy to the mammography apparatus 10. In the mammography apparatus 10, the controller 20 emits the radiation R having the second energy from the radiation source 37R toward the breast based on the instruction input from the console 12, and the first high-energy image is captured by the radiation detector 28. In a case in which the processing of step S104 ends, the first contrast imaging processing ends.

It should be noted that the order of capturing the first low-energy image and the first high-energy image is not limited to the present embodiment, and the first high-energy image may be captured before the first low-energy image. That is, the order of the processing of step S102 and the processing of step S104 may be switched.

In a case in which the first contrast imaging processing shown in FIG. 9 ends as described above, the first contrast imaging processing in step S14 shown in FIG. 8 ends. It should be noted that the controller 50 may notify the user that the first contrast imaging ends.

In next step S16, the mammography apparatus 10 moves the grid 27 from the insertion position to the retreat position and causes the grid 27 to retreat from between the radiation source 37R and the radiation detector 28 by using the grid movement unit 31 (see FIGS. 3 and 4A).

In next step S18, the mammography apparatus 10 moves the radiation source 37R to the second position by using the radiation source movement unit 39 (see FIGS. 3 and 4A).

It should be noted that the order of the processing of step S16 and the processing of step S18 may be switched, or the processing of step S16 and the processing of step S18 may be performed in parallel.

In next step S20, the console 12 performs the second contrast imaging processing for performing the second contrast imaging described above by the mammography apparatus 10. As described above, a flow of the second contrast imaging processing is the same as that of the first contrast imaging processing, and the second contrast imaging processing shown in FIG. 9 is performed by the console 12.

Specifically, in the second contrast imaging processing, in step S100 of FIG. 9, the controller 50 determines whether or not the irradiation instruction of the radiation R is received. A negative determination is made in the determination in step S100 until the irradiation instruction is received. On the other hand, in a case in which the irradiation instruction is received, a positive determination is made in the determination in step S100, and the processing proceeds to step S102.

In step S102, the controller 50 outputs the instruction to emit the radiation R having the first energy to the mammography apparatus 10. In the mammography apparatus 10, the second low-energy image is captured by the radiation detector 28.

In next step S104, the controller 50 outputs the instruction to emit the radiation R having the second energy to the mammography apparatus 10. In the mammography apparatus 10, the second high-energy image is captured by the radiation detector 28. In a case in which the processing of step S104 ends, the second contrast imaging processing ends.

In a case in which the second contrast imaging processing shown in FIG. 9 ends as described above, the second contrast imaging processing in step S20 shown in FIG. 8 ends. It should be noted that the controller 50 may notify the user that the second contrast imaging ends.

Figure 10:
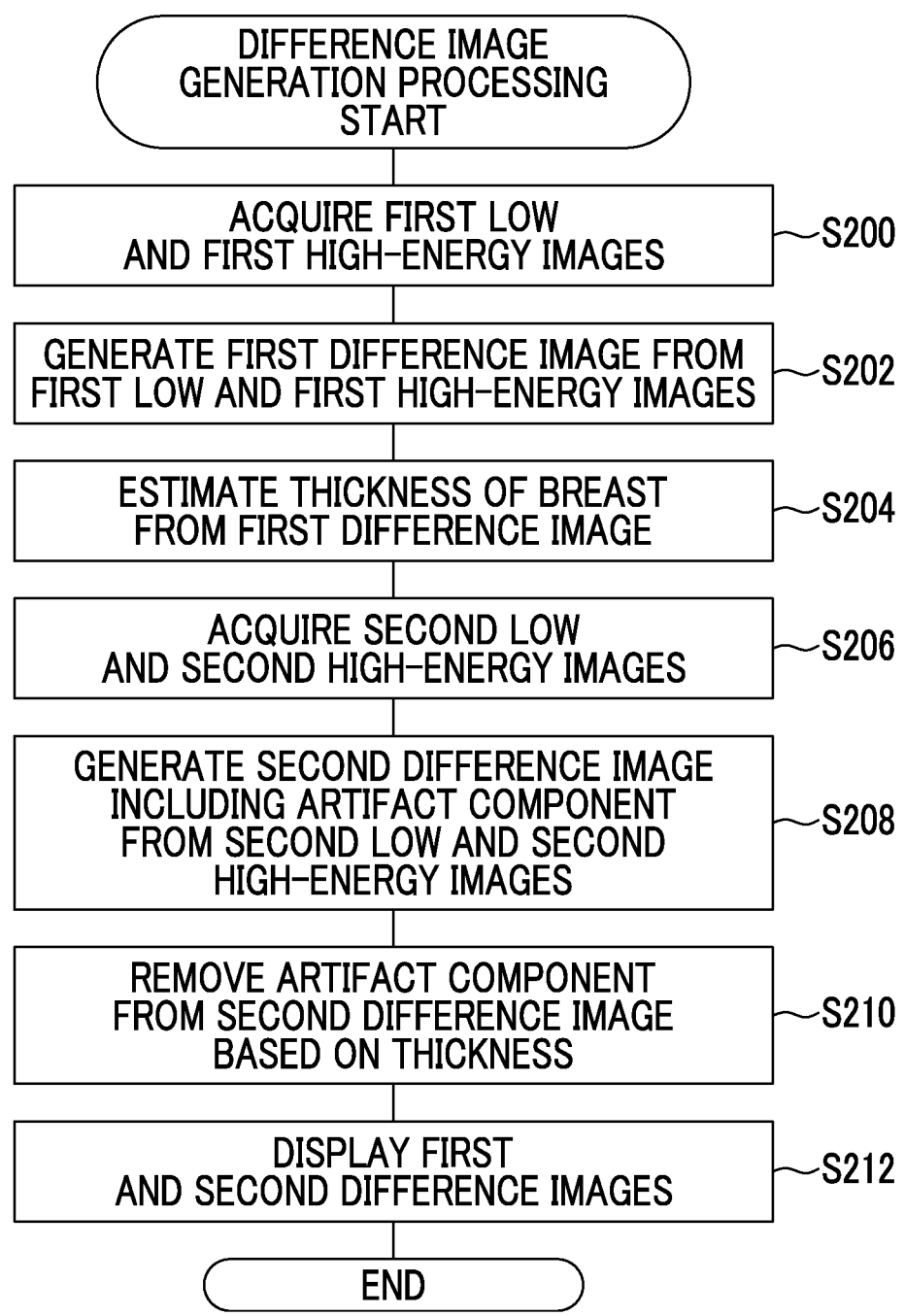
FIG. 10 is a flowchart showing an example of a flow of difference image generation processing executed in the contrast imaging according to the embodiment.

In next step S22, the console 12 performs the difference image generation processing shown in FIG. 10. In the console 12 according to the present embodiment, as an example, the CPU 50A of the controller 50 executes the difference image generation program 51B stored in the ROM 50B, thereby executing the difference image generation processing whose example is shown in FIG. 10. FIG. 10 shows a flowchart showing an example of a flow of the difference image generation processing executed in the console 12 according to the present embodiment.

In step S200, the first acquisition unit 60 acquires the first low-energy image and the first high-energy image obtained by the first contrast imaging, as described above.

In next step S202, the first difference image generation unit 64 generates the first difference image from the first low-energy image and the first high-energy image. As described above, the first difference image generation unit 64 according to the present embodiment generates the image data of the first difference image by subtracting the image data obtained by multiplying the first low-energy image by the predetermined coefficient from the image data obtained by multiplying the first high-energy image by the predetermined coefficient for each corresponding pixel.

In next step S204, the thickness estimation unit 66 estimates the thickness of the breast based on the first difference image generated in step S204. As described above, the thickness estimation unit 66 according to the present embodiment derives the thickness of the breast by calculating a coefficient that eliminates the contrast between the mammary gland and the fat in the first difference image.

As described above, the thickness of the breast is estimated from the first low-energy image and the first high-energy image obtained by the first contrast imaging using the grid by pieces of processing of steps S200 to S204.

In next step S206, the second acquisition unit 62 acquires the second low-energy image and the second high-energy image obtained by the second contrast imaging, as described above.

In next step S208, the second difference image generation unit 68 generates the second difference image including the artifact component from the second low-energy image and the second high-energy image. As described above, the second difference image generation unit 68 according to the present embodiment generates the image data of the second difference image by subtracting the image data obtained by multiplying the second low-energy image by the predetermined coefficient from the image data obtained by multiplying the second high-energy image by the predetermined coefficient for each corresponding pixel.

In next step S210, the second difference image generation unit 68 removes the artifact component from the second difference image generated in step S208 based on the thickness of the breast estimated in step S204. As described above, the second difference image generation unit 68 according to the present embodiment selects the low-frequency removal filter corresponding to the thickness of the breast estimated by the thickness estimation unit 66 from among the plurality of low-frequency removal filters prepared in accordance with the thickness of the breast, and applies the selected low-frequency removal filter to the second difference image to remove the scattered ray component and the oblique incidence component.

In next step S212, the display controller 70 performs control of displaying the first difference image generated in step S202 and the second difference image from which the artifact component has been removed in step S210 on the display unit 58.

It should be noted that a display form in which the first difference image and the second difference image are displayed on the display unit 58 is not particularly limited. For example, a form may be adopted in which the second difference image before removing the artifact component, that is, the second difference image including the artifact component generated by the processing of step S208 is displayed on the display unit 58. In addition, the first difference image and the second difference image may be displayed side by side for medical use without being superimposed, or may be displayed side by side in a partially superimposed state. Alternatively, a form may be adopted in which any one of the first difference image or the second difference image is displayed on the display unit 58 to be switchable in accordance with the instruction of the user. It should be noted that a form may be adopted in which the first low-energy image, the first high-energy image, the first difference image, the second low-energy image, the second high-energy image, the second difference image including the artifact component, the second difference image from which the artifact component has been removed, and the like are stored in the storage unit 52 of the console 12, picture archiving and communication systems (PACS), or the like.

In a case in which the processing of step S212 ends as described above, the difference image generation processing shown in FIG. 10 ends, and the difference image generation processing of step S22 shown in FIG. 8 ends.

In a case in which the contrast imaging being performed is the stereo imaging for biopsy, the user interprets the first difference image and the second difference image displayed on the display unit 58, and collects a lesion while checking the position of the lesion.

In next step S24, the compression of the breast is released. Specifically, the controller 50 outputs an instruction to the mammography apparatus 10 to move the compression plate 40 in a direction away from the imaging table 30. In the mammography apparatus 10, the controller 50 moves the compression plate 40 in the direction away from the imaging table 30 based on the input instruction. As a result, the compression of the breast is released. It should be noted that the release of the breast compression may be performed in accordance with the instruction of the user, or may be performed automatically in accordance with the end of the contrast imaging.

In next step S26, the mammography apparatus 10 moves the grid 27 to the insertion position and inserts the grid 27 between the radiation source 37R and the radiation detector 28 by using the grid movement unit 31. In the present embodiment, the insertion position of the grid 27 is an initial position. Therefore, the mammography apparatus 10 moves the grid 27, which is moved to the retreat position after the second contrast imaging, to the insertion position that is the initial position by using the grid movement unit 31.

In next step S28, the mammography apparatus 10 moves the radiation source 37R to the first position by using the radiation source movement unit 39. In the present embodiment, for the radiation source 37R, the first position is the initial position. Therefore, the mammography apparatus 10 moves the radiation source 37R, which is moved to the second position after the second contrast imaging, to the first position that is the initial position by using the radiation source movement unit 39.

In a case in which the processing of step S28 ends, a series of processing related to the contrast imaging according to the embodiment shown in FIG. 8 ends.

As described above, according to the present embodiment, the second difference image from which the artifact component has been removed is obtained based on the thickness of the breast estimated from the first difference image indicating the difference between the first high-energy image and the first low-energy image in which the artifact components are suppressed by the grid 27. Therefore, according to the present embodiment, it is possible to obtain the difference image in which the contrast medium is clearly reflected and the artifact component is suppressed.

It should be noted that the embodiment described above is an example, and various modification examples are possible. For example, the following modification examples may be used.

Modification Example 1: Modification Example of Difference Image Generation Processing In the difference image generation processing (see FIG. 10) of the form described above, the form has been described in which the artifact component has been removed from the second difference image, but a form will be described in the present modification example in which the artifact components are removed from the second low-energy image and the second high-energy image.

The second difference image generation unit 68 according to the present embodiment removes the artifact component from each of the second low-energy image and the second high-energy image based on the thickness of the breast estimated by the thickness estimation unit 66.

It should be noted that the method of removing the artifact component from the second low-energy image and the method of removing the artifact component from the second high-energy image by the second difference image generation unit 68 are not particularly limited. For example, as in the method of removing the artifact component from the second difference image, the second difference image generation unit 68 removes the artifact component by applying the low-frequency removal filter corresponding to the scattered ray component and the oblique incidence component corresponding to the thickness of the breast to each of the second low-energy image and the second high-energy image. It should be noted that the low-frequency removal filters applied to the second low-energy image and the low-frequency removal filter applied to the second high-energy image may be the same or different.

Figure 11:
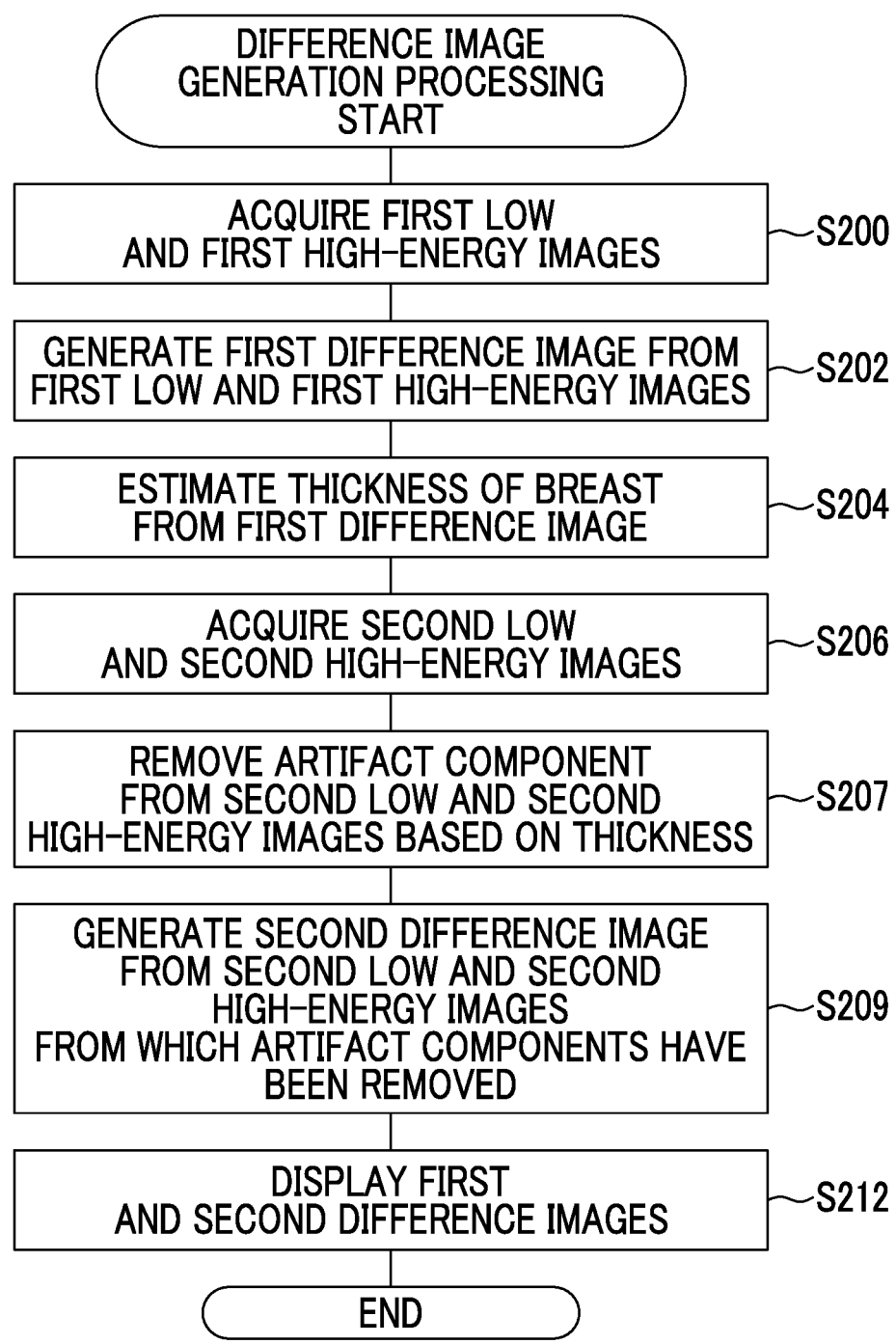
FIG. 11 is a flowchart showing an example of a flow of the difference image generation processing executed in the contrast imaging according to Modification Example 1.

FIG. 11 shows a flowchart showing an example of a flow of the difference image generation processing according to the present modification example. The difference image generation processing shown in FIG. 11 is different from the difference image generation processing (see FIG. 10) of the embodiment described above in that pieces of processing of steps S207 and S209 are provided instead of steps S208 and S210.

In step S207 of FIG. 11, the second difference image generation unit 68 removes the artifact component from each of the second low-energy image and the second high-energy image generated in step S206 based on the thickness of the breast estimated in step S204. As described above, the second difference image generation unit 68 selects the low-frequency removal filter corresponding to the thickness of the breast estimated by the thickness estimation unit 66 from among the plurality of low-frequency removal filters prepared in accordance with the thickness of the breast, and applies the selected low-frequency removal filter to the second low-energy image to remove the scattered ray component and the oblique incidence component. In addition, the second difference image generation unit 68 selects the low-frequency removal filter corresponding to the thickness of the breast estimated by the thickness estimation unit 66 from among the plurality of low-frequency removal filters prepared in accordance with the thickness of the breast, and applies the selected low-frequency removal filter to the second high-energy image to remove the scattered ray component and the oblique incidence component.

In next step S209, the second difference image generation unit 68 generates the second difference image from which artifact component has been removed, from the second low-energy image and the second high-energy image from which the artifact components have been removed in step S207. The second difference image generation unit 68 generates the image data of the second difference image from which the artifact component has been removed, by subtracting the image data obtained by multiplying the second low-energy image from which the artifact component has been removed by the predetermined coefficient from the image data obtained by multiplying the second high-energy image from which the artifact component has been removed by the predetermined coefficient for each corresponding pixel.

Thus, according to the present modification example, since the second difference image is generated from the second low-energy image and the second high-energy image from which the artifact components have been removed, the generated second difference image is the second difference image from which the artifact component has been removed.

Modification Example 2: Tomosynthesis Imaging

Although the form has been described in which the technology of the present disclosure is applied to the stereo imaging in the form described above, a form will be described in which the technology of the present disclosure is applied to tomosynthesis imaging in the present modification example.

Figure 12:
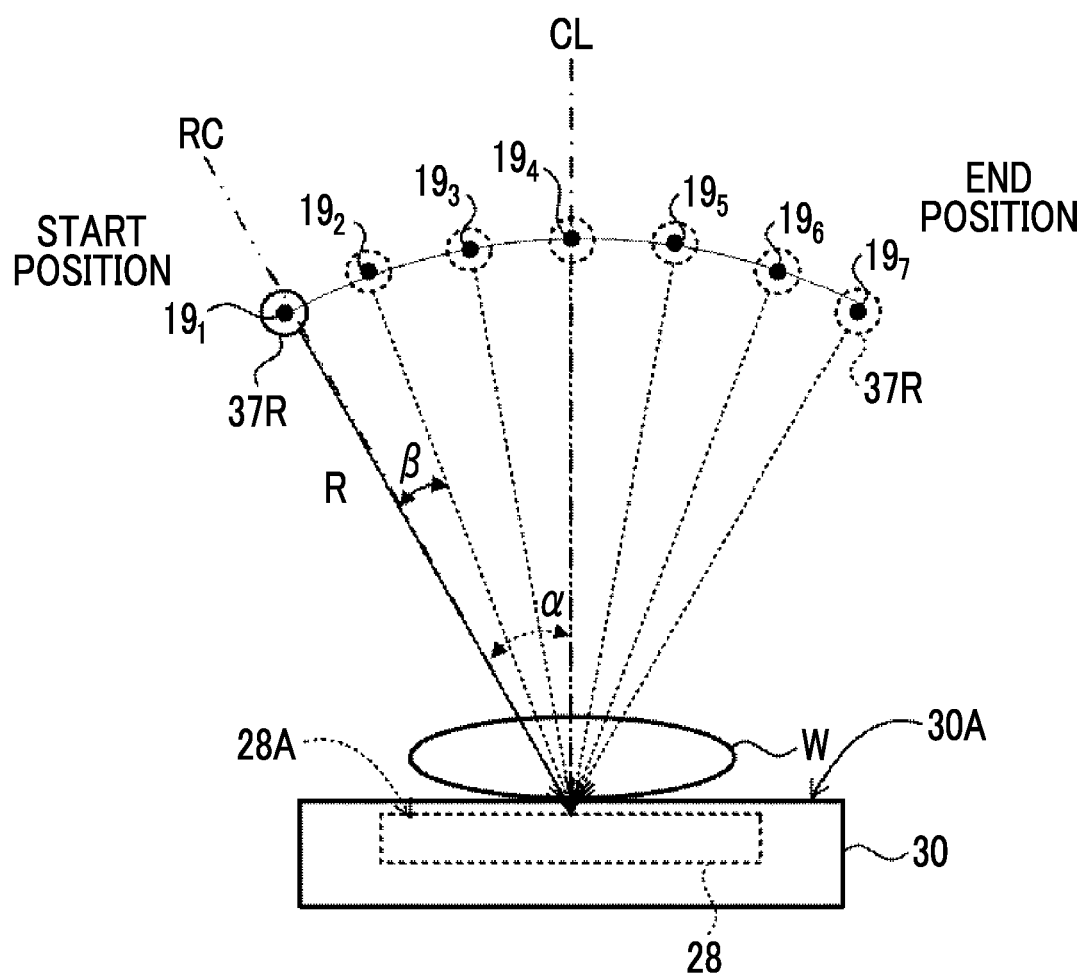
FIG. 12 is a diagram for describing tomosynthesis imaging according to Modification Example 2.

The mammography apparatus 10 according to the present embodiment has a function of performing the tomosynthesis imaging. In a case in which the tomosynthesis imaging is performed in the mammography apparatus 10, the radiation source 37R is sequentially moved to each of a plurality of irradiation positions with different irradiation angles due to the rotation of the arm part 32. The radiation source 37R has a radiation tube (not shown) that generates the radiation R, and the radiation tube is moved to each of the plurality of irradiation positions in accordance with the movement of the radiation source 37R. FIG. 12 shows a diagram for describing an example of the tomosynthesis imaging. It should be noted that, in FIG. 12, the compression plate 40 is not shown. In the present embodiment, as shown in FIG. 12, the radiation source 37R is moved to the irradiation position $19_t$ (t=1, 2, . . . , the maximum value in FIG. 12 is 7) at which the irradiation angles differ by each predetermined angle β, in other words, a position at which the irradiation angle of the radiation R with respect to the detection surface 28A of the radiation detector 28 differs. At each irradiation position $19_t$, the radiation R is emitted from the radiation source 37R toward the breast W in accordance with the instruction of the console 12, and the radiation image is captured by the radiation detector 28. In the radiography system 1, in a case in which the tomosynthesis imaging is performed by moving the radiation source 37R to each irradiation position $19_t$ to capture the radiation image at each irradiation position $19_t$, seven radiation images are obtained in the example of FIG. 12. It should be noted that, in the following description, the radiation image captured at each irradiation position $19_t$ in the tomosynthesis imaging is also referred to as a "projection image" in a case of being distinguished from other radiation images.

It should be noted that, as shown in FIG. 12, the irradiation angle of the radiation R refers to an angle α formed by the normal line CL of the detection surface 28A of the radiation detector 28, and the radiation axis RC. The radiation axis RC is an axis that connects a focal point of the radiation source 37R at each irradiation position $19_t$ and a preset position, such as the center of the detection surface 28A. In addition, here, the detection surface 28A of the radiation detector 28 is a substantially parallel surface to an imaging surface 30A.

In a case of the contrast imaging and the tomosynthesis imaging, the mammography apparatus 10 according to the present embodiment captures the projection image, which is the first low-energy image, and the projection image, which is the first high-energy image, in a state in which the radiation source 37R is disposed at the irradiation position 19₄, as the first contrast imaging. In addition, the mammography apparatus 10 captures the projection image, which is the second low-energy image, and the projection image, which is the second high-energy image, at each irradiation position $19_t$ (t≠4) in a state in which the radiation source 37R is disposed at each of the irradiation positions 19₁ to 19₃ and 19₅ to 19₇, as the second contrast imaging. That is, in the example shown in FIG. 12, in a case of the contrast imaging and the tomosynthesis imaging, a set of the first low-energy image and the first high-energy image, and six sets of the second low-energy image and the second high-energy image are obtained.

Figure 13:
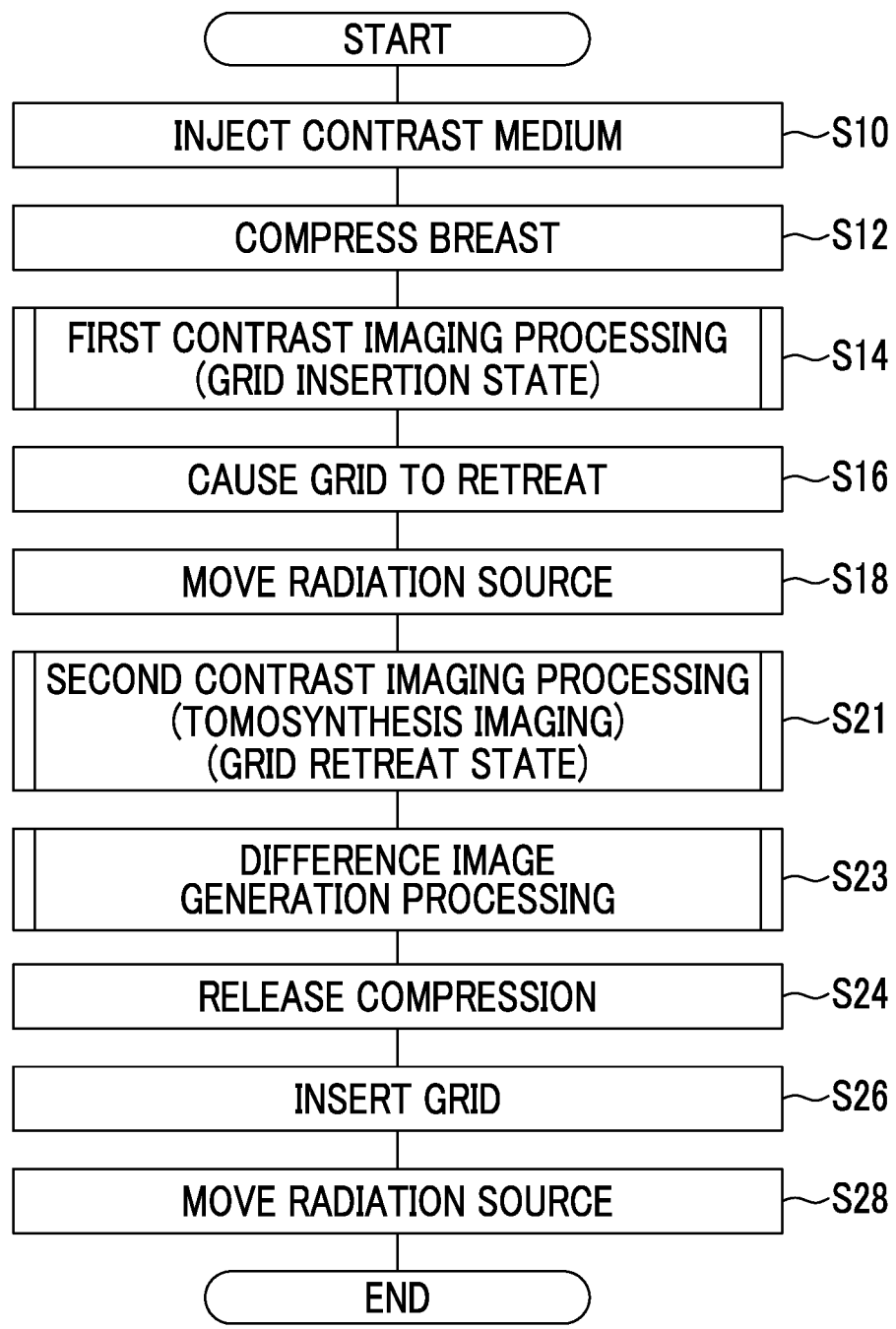
FIG. 13 is a flowchart showing an example of a flow of the contrast imaging by the radiography system according to Modification Example 2.

FIG. 13 shows a flowchart showing an example of a flow of the contrast imaging by the radiography system 1 according to the present modification example. The flow of the contrast imaging in the present modification example is different from the flow of the contrast imaging according to the embodiment described above (see FIG. 8) in that processing of step S21 is provided instead of step S20, and processing of step S23 is provided instead of step S22. That is, in the present modification example, the second contrast imaging processing and the difference image generation processing are different from the second contrast imaging processing and the difference image generation processing (see FIG. 9) according to the embodiment described above.

Figure 14:
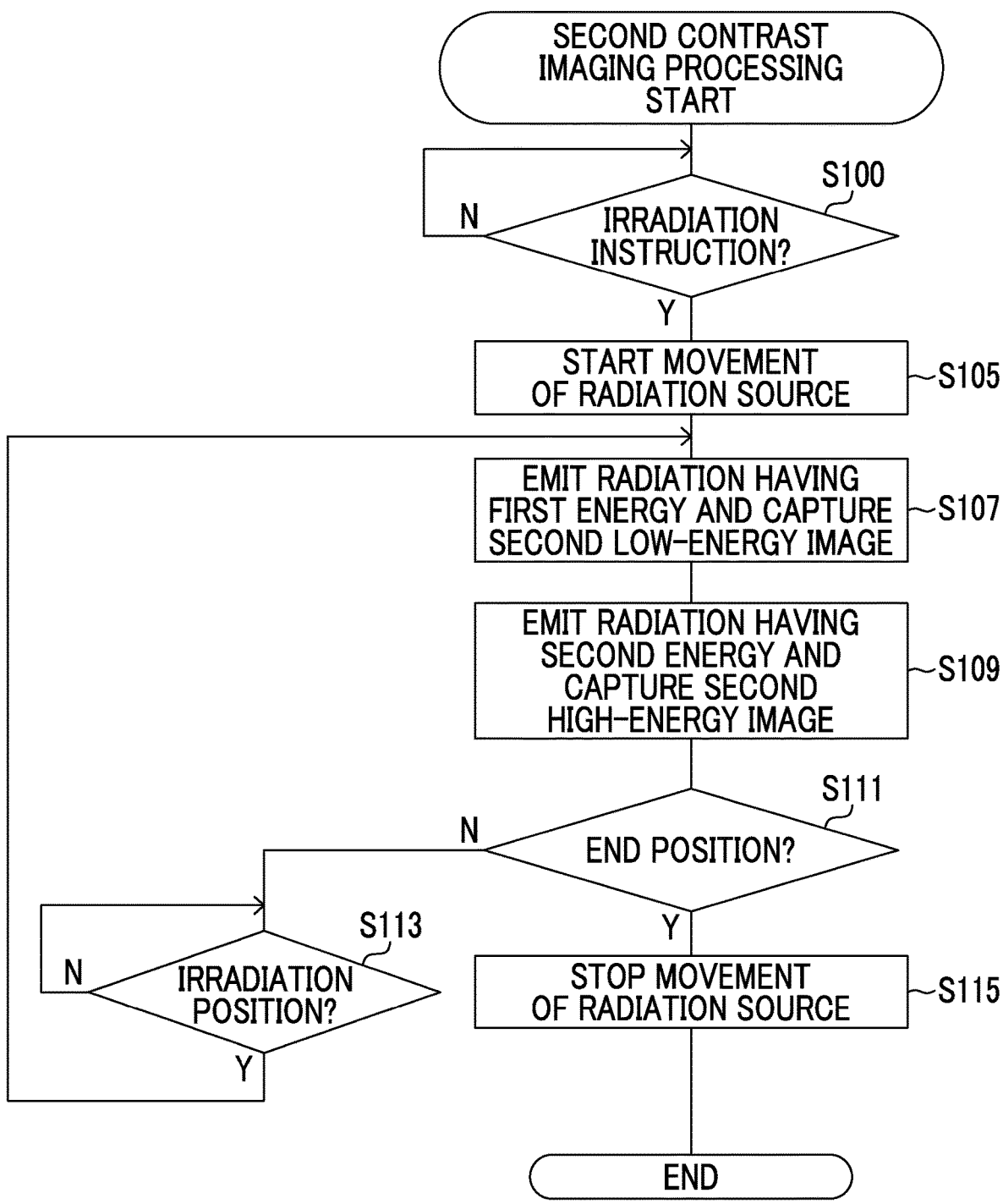
FIG. 14 is a flowchart showing an example of a flow of the contrast imaging processing executed in second contrast imaging according to Modification Example 2.

FIG. 14 shows a flowchart showing an example of a flow of the second contrast imaging processing executed in the console 12 according to the present modification example. It should be noted that, in the present modification example, in a case in which the second contrast imaging processing is started, that is, in step S18, the radiation source 37R is moved to a position at which the movement of the radiation source 37R is started in the tomosynthesis imaging, for example, to the irradiation position $19_1$ in the example shown in FIG. 12.

In step S100 of FIG. 14, the controller 50 determines whether or not the irradiation instruction of the radiation R is received, as described above. A negative determination is made in the determination in step S100 until the irradiation instruction is received. On the other hand, in a case in which the irradiation instruction is received, a positive determination is made in the determination in step S100, and the processing proceeds to step S105.

In step S105, the controller 50 starts the movement of the radiation source 37R. For example, in the example shown in FIG. 12, the movement of the radiation source 37R is started from the irradiation position $19_1$ toward the irradiation position $19_7$ which is an end position.

In step S107, the controller 50 outputs the instruction to emit the radiation R having the first energy to the mammography apparatus 10, as described above. In the mammography apparatus 10, the controller 20 emits the radiation R having the first energy from the radiation source 37R toward the breast, and the second low-energy image is captured by the radiation detector 28.

In next step S109, the controller 50 outputs the instruction to emit the radiation R having the second energy to the mammography apparatus 10, as described above. In the mammography apparatus 10, the controller 20 emits the radiation R having the second energy from the radiation source 37R toward the breast, and the second high-energy image is captured by the radiation detector 28.

In next step S111, the controller 50 determines whether or not the position of the radiation source 37R is the end position. In the example shown in FIG. 12, it is determined whether or not the position of the radiation source 37R is the irradiation position $19_7$. In other words, it is determined whether or not pieces of processing of steps S107 and S109 are performed with the position of the radiation source 37R at the irradiation position $19_7$. In a case in which the position of the radiation source 37R is not the irradiation position $19_7$, a negative determination is made in the determination in step S111, and the processing proceeds to step S113.

In step S113, the controller 50 determines whether or not the position of the moving radiation source 37R reaches the irradiation position $19_t$ (t+4). A negative determination is made in the determination in step S113 until the radiation source 37R reaches the irradiation position $19_t$ (t≠4). On the other hand, in a case in which the radiation source 37R reaches the irradiation position $19_t$ (t+4), a positive determination is made in the determination in step S113, and the processing returns to step S107, pieces of processing of steps S107 and S109 are repeated at the reached irradiation position $19_t$ (t #4).

On the other hand, in a case in which the position of the radiation source 37R is the end position in step S111, in the example shown in FIG. 12, in a case in which the position of the radiation source 37R is the irradiation position $19_7$, a positive determination is made, and the processing proceeds to step S115.

In step S115, the controller 50 stops the movement of the radiation source 37R. In a case in which the processing of step S115 ends, the second contrast imaging processing shown in FIG. 14 ends.

Figure 15:
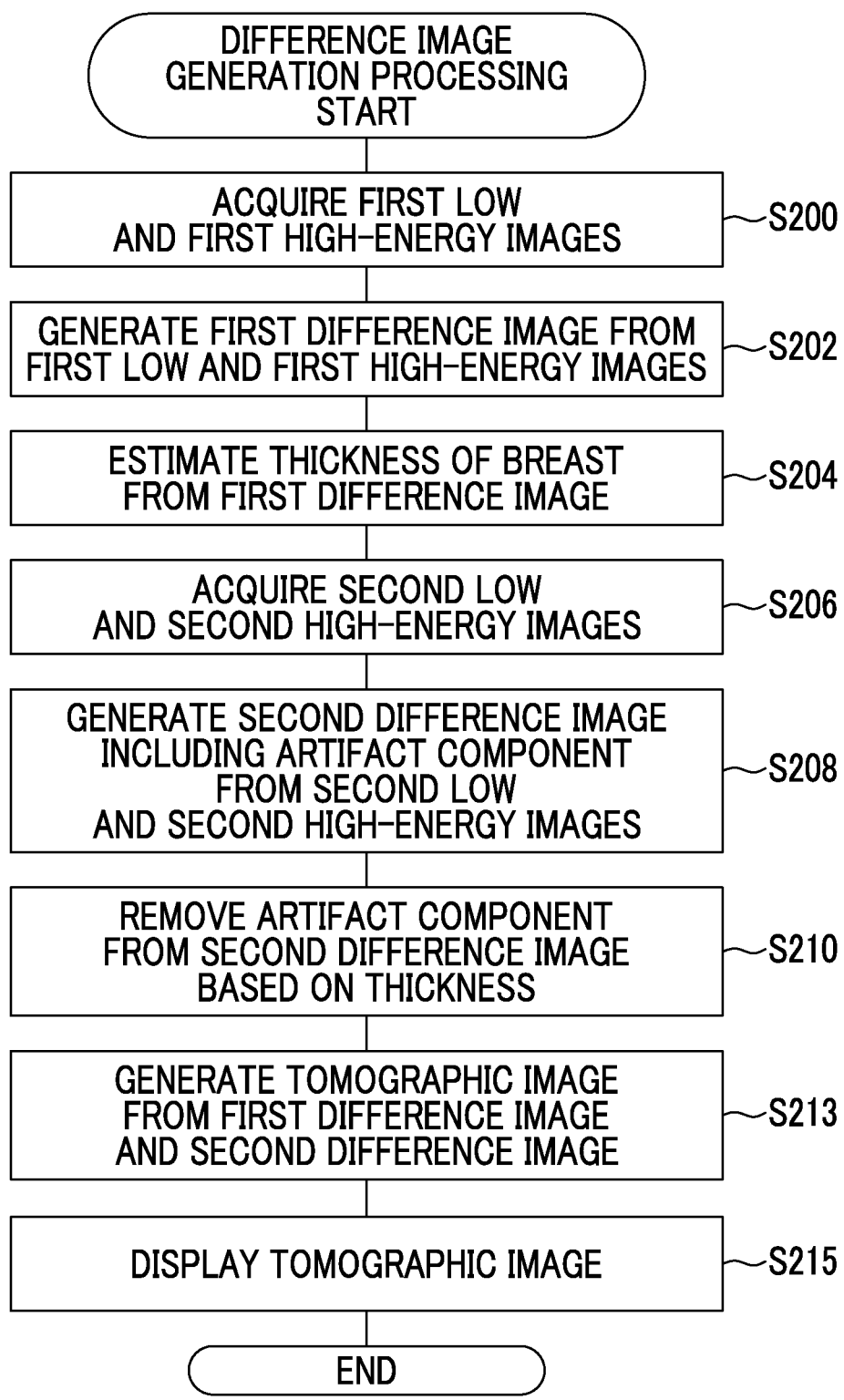
FIG. 15 is a flowchart showing an example of a flow of the difference image generation processing executed in the contrast imaging according to Modification Example 2.

On the other hand, FIG. 15 shows a flowchart showing an example of a flow of the difference image generation processing executed in the console 12 according to the present modification example.

The difference image generation processing of the present modification example shown in FIG. 15 is different from the difference image generation processing of the embodiment described above (see FIG. 10) in that pieces of processing of steps S213 and S215 are provided instead of the processing of step S212.

In step S213 of FIG. 15, the second difference image generation unit 68 further generates a tomographic image from the first difference image generated in step S202 and the plurality of second difference images generated in step S208. It should be noted that the method of generating the tomographic image from the first difference image and the plurality of second difference images by the second difference image generation unit 68 is not particularly limited. For example, the second difference image generation unit 68 can generate a plurality of tomographic images by reconstructing the first difference image and the plurality of second difference images by a back projection method, such as a filter back projection (FBP) method or a successive approximation reconstruction method.

In next step S215, the display controller 70 performs control of displaying the tomographic image generated in step S213 on the display unit 58. In a case in which the processing of step S215 ends, the difference image generation processing shown in FIG. 15 ends.

Thus, the first difference image of the present modification example is the projection image captured by using the grid 27, and is the projection image in which the artifact components including the scattered ray component and the component caused by the oblique incidence of the radiation are suppressed. In addition, each of the plurality of second difference images is the projection image from which the artifact component has been removed. Therefore, according to the present modification example, the tomographic image in which the artifact component is suppressed can be obtained.

It should be noted that in the present modification example, as in Modification Example 1, a form may be adopted in which the second difference image is generated after removing the artifact component from each of the second low-energy image and the second high-energy image.

Modification Example 3: Tomosynthesis Imaging

Figure 16:
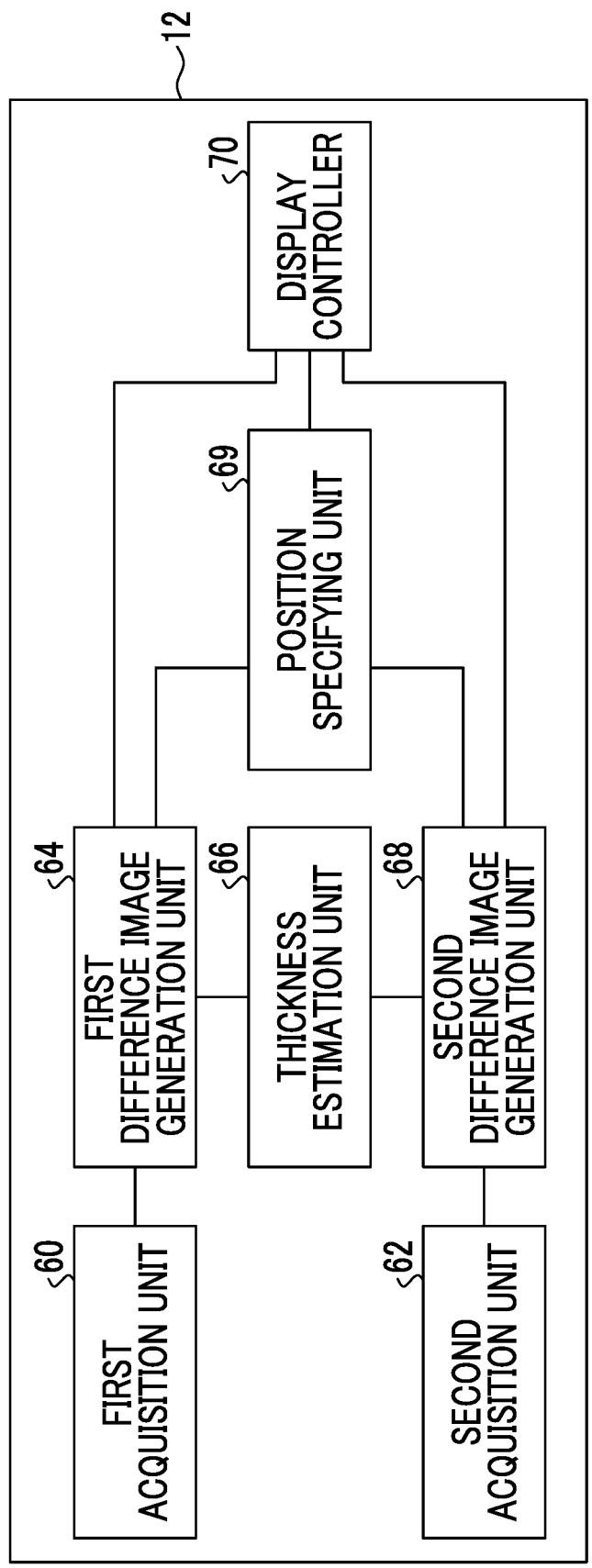
FIG. 16 is a functional block diagram showing an example of the function of the console according to Modification Example 3.

In addition to the form described above, a position of an object-of-interest dyed with the contrast medium may further be specified. FIG. 16 shows a functional block diagram of an example of a configuration of the console 12 of the present modification example. As shown in FIG. 16, the console 12 of the present modification example is different from the console 12 of the form described above in that a position specifying unit 69 is further provided.

The position specifying unit 69 has a function of specifying the position of the object-of-interest dyed with the contrast medium, more specifically, the position in a depth direction from the first difference image and the second difference image. Since both the first difference image and the second difference image are images in which the mammary gland tissue has been removed and the contrast medium is enhanced as described above, the object-of-interest, such as a tumor dyed with the contrast medium, is easily detected. The position specifying unit 69 detects the object-of-interest from each of the first difference image and the second difference image. It should be noted that the method of detecting the object-of-interest from each of the first difference image and the second difference image by the position specifying unit 69 is not particularly limited. For example, the position specifying unit 69 may detect the object-of-interest by applying a known computer-aided diagnosis (CAD) algorithm to each of the first difference image and the second difference image.

In addition, the position specifying unit 69 specifies the position of the object-of-interest in the depth direction, that is, a height from the detection surface 28A of the radiation detector 28 from the position of the object-of-interest in the first difference image and the position of the object-of-interest in the second difference image. It should be noted that the method of specifying the position of the object-of-interest in the depth direction by the position specifying unit 69 is also not particularly limited. For example, the position specifying unit 69 may specify the position of the object-of-interest in the depth direction from the position of the object-of-interest in the first difference image and the position of the object-of-interest in the second difference image by a method that applies triangular survey by stereo matching. The position specifying unit 69 outputs the specified position of the object-of-interest in the depth direction to the display controller 70.

As an example, in the console 12 according to the present embodiment, the CPU 50A of the controller 50 also functions as the position specifying unit 69 by the CPU 50A executing the difference image generation program 51B stored in the ROM 50B.

Figure 17:
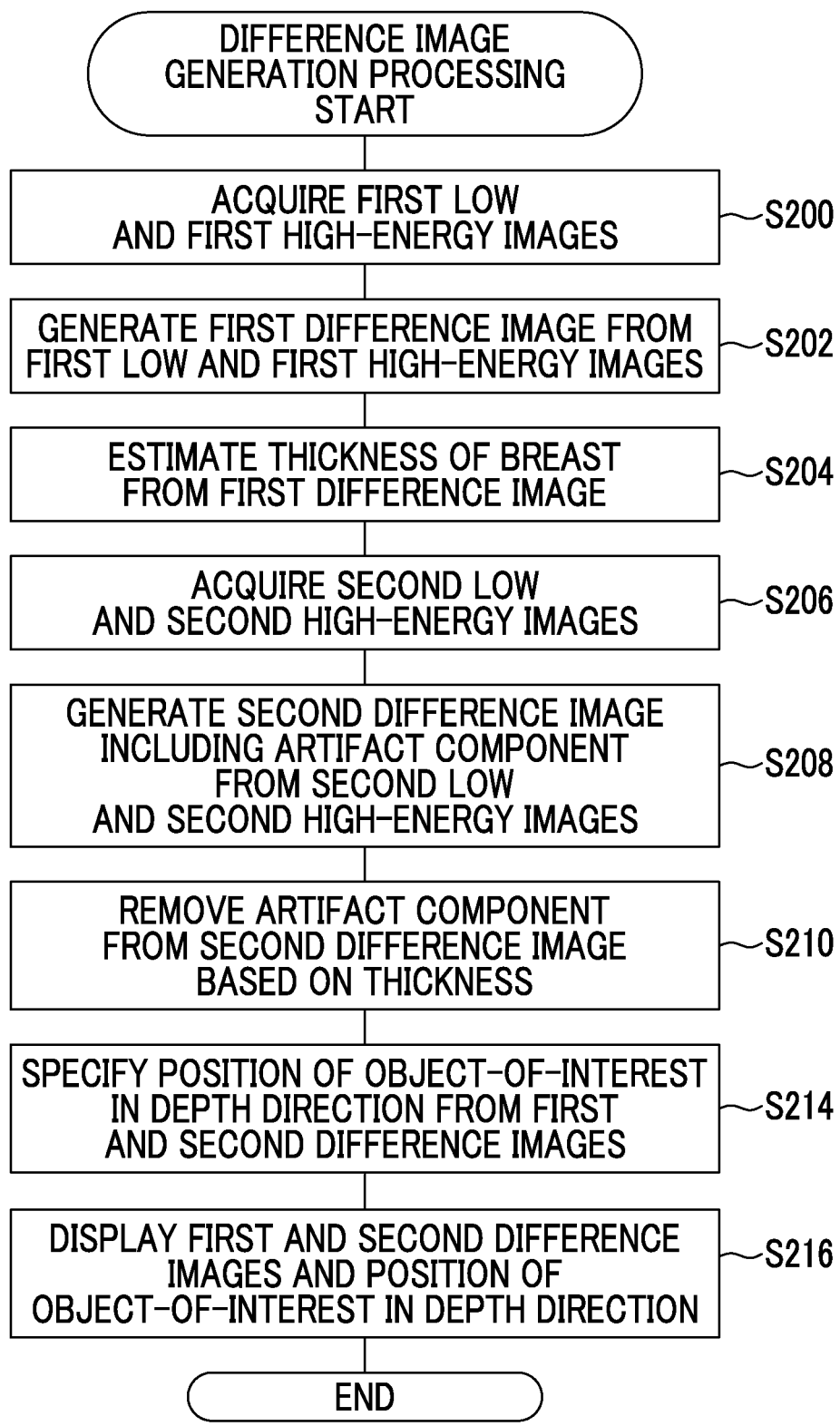
FIG. 17 is a flowchart showing an example of a flow of the difference image generation processing executed in the contrast imaging according to Modification Example 3.

Further, the difference image generation processing of specifying the position of the object-of-interest, more specifically, the position in the depth direction will be described. FIG. 17 shows a flowchart showing an example of a flow of the difference image generation processing according to the present modification example. The difference image generation processing shown in FIG. 17 is different from the difference image generation processing (see FIG. 10) of the embodiment described above in that pieces of processing of steps S214 and S216 are provided instead of step S212.

In step S214 of FIG. 17, as described above, the position specifying unit 69 specifies the position of the object-of-interest dyed with the contrast medium in the depth direction from the first difference image generated in step S202 and the second difference image generated in step S208.

In next step S216, the display controller 70 performs control of displaying the first difference image generated in step S202, the second difference image from which the artifact component has been removed in step S210, and the position of the object-of-interest in the depth direction specified in step S214 on the display unit 58.

It should be noted that the display form in which the position of the object-of-interest in the depth direction is displayed on the display unit 58 is not particularly limited. For example, information indicating the position of the object-of-interest in the depth direction may be displayed by being superimposed on the first difference image and the second difference image. It should be noted that a form may be adopted in which the position of the object-of-interest in the depth direction is associated with at least one of the first low-energy image, the first high-energy image, the first difference image, the second low-energy image, the second high-energy image, the second difference image including the artifact component, the second difference image from which the artifact component has been removed, or the like, and is stored in the storage unit 52 of the console 12, picture archiving and communication systems (PACS), or the like.

In a case in which the processing of step S216 ends as described above, the difference image generation processing shown in FIG. 17 ends.

As described above, according to the present modification example, the position of the object-of-interest in the depth direction is derived by using the first difference image in which the artifact component is suppressed by using the grid 27 and the second difference image in which the artifact component has been removed in accordance with the thickness of the breast, so that the derivation accuracy can be improved.

It should be noted that, in the present modification example, in a case in which the tomosynthesis imaging is performed as in Modification Example 3 described above, in which a case of performing the stereo imaging is described, the position specifying unit 69 need only derive the position of the object-of-interest in the depth direction from the generated tomographic image. For example, the position specifying unit 69 may need only detect the object-of-interest from each of the plurality of tomographic images to specify the position of the object-of-interest in the depth direction based on the height of the tomographic image in which the object-of-interest is detected.

As described above, the mammography apparatus 10 according to each form described above performs the imaging in which the low-energy image is acquired by the radiation detector 28 by emitting the radiation having the first energy from the radiation source 37R to the subject into which the contrast medium has been injected, and the imaging in which the high-energy image is acquired by the radiation detector 28 by emitting the radiation having the second energy higher than the first energy from the radiation source 37R to the subject into which the contrast medium has been injected.

The console 12 processes the radiation image captured by the mammography apparatus 10. The first acquisition unit 60 acquires the first low-energy image and the first high-energy image captured by the mammography apparatus 10 in a state in which the grid 27 for removing the scattered rays is inserted between the radiation source 37R and the radiation detector 28, and the radiation source 37R is disposed at the first position at which the incidence direction of the radiation is the normal direction with respect to the grid 27. The second acquisition unit 62 acquires the second low-energy image and the second high-energy image captured by the mammography apparatus 10 in a state in which the grid 27 retreats from between the radiation source 37R and the radiation detector 28, and the radiation source 37R is disposed at the second position different from the first position. The thickness estimation unit 66 estimates the thickness of the subject from the first low-energy image and the first high-energy image. The second difference image generation unit 68 generates the second difference image indicating the difference between the second high-energy image and the second low-energy image from the second low-energy image and the second high-energy image based on the estimated thickness.

Thus, the console 12 according to each form described above estimates the thickness of the breast from the first low-energy image and the first high-energy image captured by using the grid 27. In addition, the console 12 generates the second difference image from which the artifact component has been removed, from the second low-energy image and the second high-energy image captured without using the grid 27 based on the estimated thickness of the breast.

In a case in which the oblique incidence of the radiation is performed on the radiation detector 28, in other words, in a case in which the radiation source 37R is the position different from the first position at which the incidence direction of the radiation is the normal direction, the imaging using the grid 27 cannot be performed. However, with the console 12 according to each form described above, it is possible to obtain the second difference image in which the artifact component is suppressed, from the second low-energy image and the second high-energy image captured without using the grid 27. Therefore, with the console 12 according to each form described above, it is possible to obtain the difference image in which the contrast medium is clearly reflected and obtain artifact component is suppressed.

It should be noted that, in each form described above, the form has been described in which the second difference image from which the artifact component has been removed is generated based on the thickness of the breast, but a ratio (compositional ratio) between the fat and the mammary gland for each pixel may be further derived to correct the influence of the scattered rays.

In addition, in each form described above, the form has been described in which the difference image generation processing is performed as step S20 after the processing of step S20 in FIG. 8 ends, a timing of performing the difference image generation processing, that is, a timing of generating the first difference image and the second difference image is not limited to each form described above. For example, as soon as the first contrast imaging processing in step S14 ends, the difference image generation processing may be started in parallel with the processing of step S16 and subsequent steps. In addition, the difference image generation processing may be performed at a timing in accordance with a desire of the user after the contrast imaging.

In addition, in each form described above, the form has been described in which the breast is applied as an example of the subject according to the present disclosure, and the mammography apparatus 10 is applied as an example of the radiography apparatus according to the present disclosure, but the subject is not limited to the breast, and the radiography apparatus is not limited to the mammography apparatus. For example, the subject may be a chest, an abdomen, or the like, and a form may be adopted in which a radiography apparatus other than the mammography apparatus is applied as the radiography apparatus.

In addition, in each form described above, the form has been described in which the console 12 is an example of the image processing apparatus according to the present disclosure, but an apparatus other than the console 12 may have the function of the image processing apparatus according to the present disclosure. In other words, some or all of the functions of the first acquisition unit 60, the second acquisition unit 62, the first difference image generation unit 64, the thickness estimation unit 66, the second difference image generation unit 68, and the display controller 70 may be provided in an apparatus other than the console 12, for example, the mammography apparatus 10 or an external apparatus.

In addition, in each form described above, various processors shown below can be used as the hardware structure of processing units that execute various pieces of processing, such as the first acquisition unit 60, the second acquisition unit 62, the first difference image generation unit 64, the thickness estimation unit 66, the second difference image generation unit 68, and the display controller 70. As described above, the various processors include, in addition to the CPU which is a general-purpose processor which executes software (program) and functions as various processing units, a programmable logic device (PLD) which is a processor of which a circuit configuration can be changed after manufacture, such as a field programmable gate array (FPGA), and a dedicated electric circuit which is a processor having a circuit configuration which is designed for exclusive use in order to execute specific processing, such as an application specific integrated circuit (ASIC).

One processing unit may be composed of one of the various processors or may be composed of a combination of two or more processors of the same type or different types (for example, a combination of a plurality of FPGAs or a combination of a CPU and an FPGA). In addition, a plurality of processing units may be composed of one processor.

A first example of the configuration in which the plurality of processing units are composed of one processor is a form in which one processor is composed of a combination of one or more CPUs and software and the processor functions as the plurality of processing units, as represented by the computer, such as a client and a server. Second, as represented by a system on chip (SoC) or the like, there is a form of using a processor that realizes the function of the entire system including the plurality of processing units by one integrated circuit (IC) chip. As described above, various processing units are composed of one or more of the various processors as the hardware structure.

Further, more specifically, an electric circuit (circuitry) obtained by combining circuit elements, such as semiconductor elements, can be used as the hardware structure of the various processors.

In addition, in each embodiment described above, the aspect has been described in which the contrast imaging processing program 51A and the difference image generation program 51B are stored (installed) in advance in the ROM 50B, but the present disclosure is not limited to this. An aspect may be provided in which each of the contrast imaging processing program 51A and the difference image generation program 51B is recorded in the recording medium, such as a compact disc read only memory (CD-ROM), a digital versatile disc read only memory (DVD-ROM), and a universal serial bus (USB) memory. In addition, a form may be adopted in which each of the contrast imaging processing program 51A and the difference image generation program 51B is downloaded from an external apparatus via a network.

What is claimed is:

1. An image processing apparatus that processes a radiation image captured by a radiography apparatus including a radiation source and a radiation detector, the image processing apparatus comprising:
at least one processor that is configured to:
acquire a first low-energy image and a first high-energy image of a subject captured by the radiography apparatus in a state in which a grid for removing scattered rays is inserted between the radiation source and the radiation detector, and the radiation source is disposed at a first position at which an incidence direction of the radiation is a normal direction with respect to the grid;
acquire a second low-energy image and a second high-energy image of the subject captured by the radiography apparatus in a state in which the grid retreats from between the radiation source and the radiation detector, and the radiation source is disposed at a second position different from the first position;
estimate a thickness of the subject from the first low-energy image and the first high-energy image; and
generate a difference image indicating a difference between the second high-energy image and the second low-energy image from the second low-energy image and the second high-energy image based on the estimated thickness,
wherein the first and second low-energy images are captured by emitting radiation having first energy from the radiation source to the subject into which a contrast medium has been injected, and
the first and second high-energy images are captured by emitting radiation having second energy higher than the first energy from the radiation source to the subject into which the contrast medium has been injected.

2. The image processing apparatus according to claim 1, wherein the processor is configured to:
remove an artifact component from each of the second high-energy image and the second low-energy image based on the thickness; and
generate the difference image from the second low-energy image and the second high-energy image from which the artifact components have been removed.

3. The image processing apparatus according to claim 1, wherein the processor is configured to:
generate the difference image from the second low-energy image and the second high-energy image; and
remove an artifact component from the difference image based on the thickness.

4. The image processing apparatus according to claim 2, wherein the artifact component is an oblique incidence component caused by oblique incidence of the radiation.

5. The image processing apparatus according to claim 2, wherein the artifact component is a scattered ray component caused by the scattered ray.

6. The image processing apparatus according to claim 1, wherein the processor is configured to estimate the thickness from a difference image indicating a difference between the first high-energy image and the first low-energy image.

7. The image processing apparatus according to claim 1, wherein the processor is configured to identify a position of an object-of-interest dyed with the contrast medium in a depth direction from a difference image indicating a difference between the first high-energy image and the first low-energy image, and the difference image indicating the difference between the second high-energy image and the second low-energy image.

8. An image processing method in which a computer executes image processing of a radiation image captured by a radiography apparatus including a radiation source and a radiation detector, the image processing method comprising:
acquiring a first low-energy image and a first high-energy image of a subject captured by the radiography apparatus in a state in which a grid for removing scattered rays is inserted between the radiation source and the radiation detector, and the radiation source is disposed at a first position at which an incidence direction of the radiation is a normal direction with respect to the grid;
acquiring a second low-energy image and a second high-energy image of the subject captured by the radiography apparatus in a state in which the grid retreats from between the radiation source and the radiation detector, and the radiation source is disposed at a second position different from the first position;
estimating a thickness of the subject from the first low-energy image and the first high-energy image; and
generating a difference image indicating a difference between the second high-energy image and the second low-energy image from the second low-energy image and the second high-energy image based on the estimated thickness,
wherein the first and second low-energy images are captured by emitting radiation having first energy from the radiation source to the subject into which a contrast medium has been injected, and
the first and second high-energy images are captured by emitting radiation having second energy higher than the first energy from the radiation source to the subject into which the contrast medium has been injected.

9. A non-transitory storage medium storing an image processing program causing a computer to execute image processing of a radiation image captured by a radiography apparatus including a radiation source and a radiation detector, the image processing comprising:
acquiring a first low-energy image and a first high-energy image of a subject captured by the radiography apparatus in a state in which a grid for removing scattered rays is inserted between the radiation source and the radiation detector, and the radiation source is disposed at a first position at which an incidence direction of the radiation is a normal direction with respect to the grid;
acquiring a second low-energy image and a second high-energy image of the subject captured by the radiography apparatus in a state in which the grid retreats from between the radiation source and the radiation detector, and the radiation source is disposed at a second position different from the first position;
estimating a thickness of the subject from the first low-energy image and the first high-energy image; and
generating a difference image indicating a difference between the second high-energy image and the second low-energy image from the second low-energy image and the second high-energy image based on the estimated thickness,
wherein the first and second low-energy images are captured by emitting radiation having first energy from the radiation source to the subject into which a contrast medium has been injected, and
the first and second high-energy images are captured by emitting radiation having second energy higher than the first energy from the radiation source to the subject into which the contrast medium has been injected.

\* \* \* \* \*